US008754198B2

(12) United States Patent
Lunder et al.

(10) Patent No.: US 8,754,198 B2
(45) Date of Patent: Jun. 17, 2014

(54) MODIFIED FOOD GRADE MICROORGANISM FOR TREATMENT OF INFLAMMATORY BOWEL DISEASE

(75) Inventors: Mojca Lunder, Ljubljana (SI); Matjaz Ravnikar, Ljubljana (SI); Borut Strukelj, Ljubljana (SI); Ales Berlec, Ziri (SI); Boris Ceh, Ljubljana (SI)

(73) Assignees: University of Ljubljana, Ljubljana (SI); Institute Jozef Stefan, Ljubljana (SI); Labena d.o.o., Ljubljana (SI)

( * ) Notice: Subject to any disclaimer, the term of this patent is extended or adjusted under 35 U.S.C. 154(b) by 0 days.

(21) Appl. No.: 13/519,408

(22) PCT Filed: Jan. 5, 2011

(86) PCT No.: PCT/EP2011/000019

§ 371 (c)(1), (2), (4) Date: Jul. 16, 2012

(87) PCT Pub. No.: WO2011/083080

PCT Pub. Date: Jul. 14, 2011

(65) Prior Publication Data

US 2012/0282700 A1 Nov. 8, 2012

(30) Foreign Application Priority Data

Jan. 7, 2010 (EP) .................................... 10000074

(51) Int. Cl.

*C07H 21/04* (2006.01)
*C07K 1/00* (2006.01)
*C07K 14/525* (2006.01)

(52) U.S. Cl.

CPC ......... *C07K 14/525* (2013.01); *C07K 2319/035* (2013.01); *C07K 2319/00* (2013.01)

USPC ....... 536/23.4; 536/23.5; 536/24.1; 536/24.2; 530/350; 530/402

(58) Field of Classification Search

None

See application file for complete search history.

(56) References Cited

U.S. PATENT DOCUMENTS

| | | | | |
|---|---|---|---|---|
| 7,993,848 | B2 * | 8/2011 | Herne | 435/7.1 |
| 2007/0276124 | A1 * | 11/2007 | Turner et al. | 530/324 |
| 2008/0274084 | A1 * | 11/2008 | Rottiers et al. | 424/93.2 |
| 2010/0310514 | A1 * | 12/2010 | Cho et al. | 424/93.2 |

FOREIGN PATENT DOCUMENTS

| | | |
|---|---|---|
| EP | 1 477 802 A1 | 11/2004 |
| WO | 97/14806 | 4/1997 |
| WO | 00/23471 | 4/2000 |
| WO | 2007/025977 | 3/2007 |

OTHER PUBLICATIONS

Hugot et al., "Etiology of the inflammatory bowel diseases", Int J Colorectal Dis., 14, 1999, pp. 2-9.
Cho , "The genetics and immunopathogenesis of inflammatory bowel disease", Nature Reviews/Immunology, vol. 8, Jun. 2008, pp. 458-466.
Schwartz et al., "Optimizing Conventional Therapy for Inflammatory Bowel Disease", Current Gastroenterology Report, 10, 2008, pp. 585-590.
Old, "Tumor Necrosis Factor (TNF)", Science Magazine, vol. 230, 1985, pp. 630-632.
Sandborn et al., "Antitumor Necrosis Factor Therapy for Inflammatory Bowel Disease: A Review of Agents, Pharmacology, Clinical Results, and Safety", Inflammatory Bowel Diseases, 1999, pp. 119-133.
de Silva et al., "TNFα in stool as marker of intestinal inflammation", The Lancet, vol. 340, 1992, p. 372.
Worledge et al., "Oral Administration of Avian Tumor Necrosis Factor Antibodies Effectively Treats Experimental Colitis in Rats", Digestive Diseases and Sciences, vol. 45, No. 12, Dec. 2000, pp. 2298-2305.
Nygren, "Alternative binding proteins: affibody binding proteins developed from a small three-helix bundle scaffold", The FEBS Journal, 275, 2008, pp. 2668-2676.
Le Loir et al., "Signal Peptide and Propeptide Optimization for Heterologous Protein Secretion in *Lactococcus lactis*", Applied and Environmental Microbiology, vol. 67, No. 9, Sep. 2001, pp. 4119-4127.
International Search Report for corresponding International Application No. PCT/EP2011/000019 dated Mar. 29, 2011.
Written Opinion of the International Searching Authority for corresponding International Application No. PCT/EP2011/000019 dated Mar. 29, 2011.

* cited by examiner

*Primary Examiner* — Shulamith H Shafer

(74) *Attorney, Agent, or Firm* — Renner, Otto, Boisselle & Sklar, LLP

(57) ABSTRACT

The present invention relates to microorganisms that express, or have attached to their surface, a TNFα binding polypeptide. Peptides expressed or attached on the surface of microorganism are more resistant to chemical and enzymatic degradation in the gastrointestinal tract. Such microorganisms are capable of binding TNFα and therefore reducing the content of free TNFα and alleviating its pro-inflammatory effects in the gut. The invention also relates to the use of such microorganisms as medicament in the treatment of inflammatory bowel disease.

5 Claims, 7 Drawing Sheets

SD-TNF (SEQ ID NO:6)
MAKKKIISAILMSTVILSAAAPLSGVYA*GS*VDNKFNKELGWAIGEIGTLPNLNHQQFRAFI
LSLWDDPSQSANLLAEAKKLNDAQAPK*EF*FDGASSAGNTNSGGSTTTITNNNSGTNSSSTT
YTVKSGDTLWGISQRYGISVAQIQSANNLKSTIIYIGQKLVLTGSASSTNSGGS

SDL-TNF (SEQ ID NO:7)
MAKKKIISAILMSTVILSAAAPLSGVYA*LEISSYCDAGS*VDNKFNKELGWAIGEIGTLPNL
NHQQFRAFILSLWDDPSQSANLLAEAKKLNDAQAPK*EF*FDGASSAGNTNSGGSTTTITNNN
SGTNSSSTTYTVKSGDTLWGISQRYGISVAQIQSANNLKSTIIYIGQKLVLTGSASSTNSG
GS

SDL-TNF A3a (SEQ ID NO:8)
MAKKKIISAILMSTVILSAAAPLSGVYA*LEISSYCDAGS*VDNKFNKELGWAIGEIGTLPNL
NHQQFRAFILSLWDDPSQSANLLAEAKKLNDAQAPK*EF*FDGASSAGNTNSGGSTTTITNNN
SGTNSSSTTYTVKSGDTLWGISQRYGISVAQIQSANNLKSTIIYIGQKLVLTGSASSTNSG
GSNNSASTTPTTSVTPAKPTSQTTVKVKSGDTLWALSVKYKTSIAQLKSWNHLSSDTIYIG
QNLIVSQSAAASNPSTGSGSTATNNSNSTSSNSNASIHKVVKGDTLWGLSQKSGSPIASIK
AWNHLSSDTILIGQYLRIK

SDL-TNF A3b (SEQ ID NO:9)
MAKKKIISAILMSTVILSAAAPLSGVYA*LEISSYCDAGS*VDNKFNKELGWAIGEIGTLPNL
NHQQFRAFILSLWDDPSQSANLLAEAKKLNDAQAPK*EF*SGGSTTTITNNNSGTNSSSTTYT
VKSGDTLWGISQRYGISVAQIQSANNLKSTIIYIGQKLVLTGSASSTNSGGSNNSASTTPT
TSVTPAKPTSQTTVKVKSGDTLWALSVKYKTSIAQLKSWNHLSSDTIYIGQNLIVSQSAAA
SNPSTGSGSTATNNSNSTSSNSNASIHKVVKGDTLWGLSQKSGSPIASIKAWNHLSSDTIL
IGQYLRIK

SDL-TNF A3c (SEQ ID NO:10)
MAKKKIISAILMSTVILSAAAPLSGVYA*LEISSYCDAGS*VDNKFNKELGWAIGEIGTLPNL
NHQQFRAFILSLWDDPSQSANLLAEAKKLNDAQAPK*EF*SGTNSSSTTYTVKSGDTLWGISQ
RYGISVAQIQSANNLKSTIIYIGQKLVLTGSASSTNSGGSNNSASTTPTTSVTPAKPTSQT
TVKVKSGDTLWALSVKYKTSIAQLKSWNHLSSDTIYIGQNLIVSQSAAASNPSTGSGSTAT
NNSNSTSSNSNASIHKVVKGDTLWGLSQKSGSPIASIKAWNHLSSDTILIGQYLRIK

Figure 7a

AcmA (SEQ ID NO:11)
>sp|A2RHZ5|ACMA_LACLM Probable N-acetylmuramidase
OS=Lactococcus lactis subsp. cremoris (strain MG1363) GN=acmA
PE=3 SV=1
MPVSRVKVKNRHLKKKTKKPLAFYKPATKFAGAVLIAGTLTTTHELLLQQTSPMVQAATNSS
EVFIESIAASAKPVADANGLYPSVMIAQAILESNWGSSQLSRAPYYNLFGIQGTYQGKSVVF
KTQEYLNGKWVTKDMPFRVYPSFNQSFQDNAYVLKTTNFGNGPYYAKAWRANAATYQDATAA
LTGRYATDPSYGASLNRIISQYNLTRFDGASSAGNTNSGGSTTTITNNNSGTNSSSTTYTVK
SGDTLWGISQRYGISVAQIQSANNLKSTIIYIGQKLVLTGSASSTNSGGSNNSASTTPTTSV
TPAKPTSQTTVKVKSGDTLWALSVKYKTSIAQLKSWNHLSSDTIYIGQNLIVSQSAAASNPS
TGSGSTATNNSNSTSSNSNASIHKVVKGDTLWGLSQKSGSPIASIKAWNHLSSDTILIGQYL
RIK

Usp45 (SEQ ID NO:12)
>sp|P22865|USP45_LACLM Secreted 45 kDa protein OS=Lactococcus
lactis subsp. cremoris (strain MG1363) GN=usp45 PE=1 SV=3
MKKKIISAILMSTVILSAAAPLSGVYADTNSDIAKQDATISSAQSAKAQAQAQVDSLQSKVD
SLQQKQTSTKAQIAKIESEAKALNAQIATLNESIKERTKTLEAQARSAQVNSSATNYMDAVV
NSKSLTDVIQKVTAIATVSSANKQMLEQQEKEQKELSQKSETVKKNYNQFVSLSQSLDSQAQ
ELTSQQAELKVATLNYQATIATAQDKKQALLDEKAAAEKAAQEAAKKQAAYEAQQKEAAQAQ
AASTAATAKAVEAATSSASASSSQAPQVSTSTDNTTSNASASNSSNSSSNSSSSSSSSSSSS
SSSSNSNAGGNTNSGTSTGNTGGTTTGGSGINSSPIGNPYAGGGCTDYVWQYFAAQGIYIRN
IMPGNGGQWASNGPAQGVLHVVGAAPGVIASSFSADFVGYANSPYGHVAIVKSVNSDGTITI
KEGGYGTTWWGHERTVSASGVTFLMPN WHEREIN:
Secretion signals are underlined
(signal sequence derived from Usp45 protein;
MAKKKIISAILMSTVILSAAAPLSGVYA)(SEQ ID NO. 21)

Synthetic propeptides are *underlined + italics*.
(LEISSYCDA)(SEQ ID NO. 13)

TNFα binding domains are double underlined.
(affibody Z00185 from WO2006/092338;
VDNKFNKELGWAIGEIGTLPNLNHQQFRAFILSLWDDPSQSANLLAEAKKLNDAQAPK)
(SEQ ID NO. 22)

Surface attachment domains are dotted.
(derived from AcmA; LysM repeats of the surface attachment
domain are shown as dashed)

Spacers are in *italics*.
(GS and EF)

SEQUENCE LISTING

```
<160> NUMBER OF SEQ ID NOS: 22

<210> SEQ ID NO 1
<211> LENGTH: 531
<212> TYPE: DNA
<213> ORGANISM: Artificial
```

<220> FEATURE:
<223> OTHER INFORMATION: Gene construct comprising signal peptide coding sequence, TNFalpha affinity domain coding sequence and surface attachment domain coding sequence.

<400> SEQUENCE: 1

```
atggctaaaa aaaagattat ctcagctatt ttaatgtcta cagtgatact ttctgctgca     60

gccccgttgt caggtgttta cgctggatcc gttgataaca aatttaataa agaacttggt    120

tgggctattg gagaaatcgg aactcttcca aacttaaatc accaacaatt ccgtgctttt    180

attctttcac tttgggatga tccatcacaa tcagctaacc ttttggctga agctaaaaaa    240

cttaacgatg ctcaagctcc aaaagaattc tttgacggag cttcttcagc tggaaatact    300

aattctggtg gctcgacaac cacaattacg aataataatt ctggaaccaa tagcagttca    360

actacttata ccgtcaaatc tggtgatact ctttggggaa tctcacaaag atatggaatt    420

agtgtcgctc aaattcaaag tgcgaataat cttaaaagta ccattatcta cattggtcaa    480

aaacttgtac tgacaggttc agcttcttct acaaattccg gtggttccta a             531
```

<210> SEQ ID NO 2
<211> LENGTH: 558
<212> TYPE: DNA
<213> ORGANISM: Artificial
<220> FEATURE:
<223> OTHER INFORMATION: Gene construct comprising signal peptide coding sequence, TNFalpha affinity domain coding sequence and surface attachment domain coding sequence.

<400> SEQUENCE: 2

```
atggctaaaa aaaagattat ctcagctatt ttaatgtcta cagtgatact ttctgctgca     60

gccccgttgt caggtgttta cgctcttgaa atctcatcat actgtgatgc tggatccgtt    120

gataacaaat ttaataaaga acttggttgg gctattggag aaatcggaac tcttccaaac    180

ttaaatcacc aacaattccg tgcttttatt ctttcacttt gggatgatcc atcacaatca    240

gctaaccttt tggctgaagc taaaaaactt aacgatgctc aagctccaaa agaattcttt    300

gacggagctt cttcagctgg aaatactaat tctggtggct cgacaaccac aattacgaat    360

aataattctg gaaccaatag cagttcaact acttataccg tcaaatctgg tgatactctt    420

tggggaatct cacaaagata tggaattagt gtcgctcaaa ttcaaagtgc gaataatctt    480

aaaagtacca ttatctacat tggtcaaaaa cttgtactga caggttcagc ttcttctaca    540

aattccggtg gttcctaa                                                  558
```

<210> SEQ ID NO 3
<211> LENGTH: 975
<212> TYPE: DNA
<213> ORGANISM: Artificial
<220> FEATURE:
<223> OTHER INFORMATION: Gene construct comprising signal peptide coding sequence, TNFalpha affinity domain coding sequence and surface attachment domain coding sequence.

<400> SEQUENCE: 3

```
atggctaaaa aaaagattat ctcagctatt ttaatgtcta cagtgatact ttctgctgca     60

gccccgttgt caggtgttta cgctcttgaa atctcatcat actgtgatgc tggatccgtt    120

gataacaaat ttaataaaga acttggttgg gctattggag aaatcggaac tcttccaaac    180

ttaaatcacc aacaattccg tgcttttatt ctttcacttt gggatgatcc atcacaatca    240

gctaaccttt tggctgaagc taaaaaactt aacgatgctc aagctccaaa agaattcttt    300
```

-continued

```
gacggagctt cttcagctgg aaatactaat tctggtggct cgacaaccac aattacgaat    360

aataattctg gaaccaatag cagttcaact acttataccg tcaaatctgg tgatactctt    420

tggggaatct cacaaagata tggaattagt gtcgctcaaa ttcaaagtgc gaataatctt    480

aaaagtacca ttatctacat tggtcaaaaa cttgtactga caggttcagc ttcttctaca    540

aattcaggtg gttcaaacaa ttccgcaagc actactccaa ccacttctgt gacacctgca    600

aaaccaactt cacaaacaac tgttaaggtt aaatccggag ataccctttg ggcgctatca    660

gtaaaatata aaactagtat tgctcaattg aaaagttgga atcatttaag ttcagatacc    720

atttatattg gtcaaaatct tattgtttca caatctgctg ctgcttcaaa tccttcgaca    780

ggttcaggct caactgctac caataactca aactcgactt cttctaactc aaatgcctca    840

attcataagg tcgttaaagg agatactctc tggggacttt cgcaaaaatc tggcagccca    900

attgcttcaa tcaaggcttg gaatcattta tctagcgata ctattttaat tggtcagtat    960

ctacgaataa aataa                                                     975
```

<210> SEQ ID NO 4
<211> LENGTH: 942
<212> TYPE: DNA
<213> ORGANISM: Artificial
<220> FEATURE:
<223> OTHER INFORMATION: Gene construct comprising signal peptide coding sequence, TNFalpha affinity domain coding sequence and surface attachment domain coding sequence.

<400> SEQUENCE: 4

```
atggctaaaa aaaagattat ctcagctatt ttaatgtcta cagtgatact ttctgctgca     60

gccccgttgt caggtgttta cgctcttgaa atctcatcat actgtgatgc tggatccgtt    120

gataacaaat ttaataaaga acttggttgg gctattggag aaatcggaac tcttccaaac    180

ttaaatcacc aacaattccg tgcttttatt ctttcacttt gggatgatcc atcacaatca    240

gctaaccttt tggctgaagc taaaaaactt aacgatgctc aagctccaaa agaattctct    300

ggtggctcga caaccacaat tacgaataat aattctggaa ccaatagcag ttcaactact    360

tataccgtca aatctggtga tactctttgg ggaatctcac aaagatatgg aattagtgtc    420

gctcaaattc aaagtgcgaa taatcttaaa agtaccatta tctacattgg tcaaaaactt    480

gtactgacag gttcagcttc ttctacaaat tcaggtggtt caaacaattc cgcaagcact    540

actccaacca cttctgtgac acctgcaaaa ccaacttcac aaacaactgt taaggttaaa    600

tccggagata ccctttgggc gctatcagta aaatataaaa ctagtattgc tcaattgaaa    660

agttggaatc atttaagttc agataccatt tatattggtc aaaatcttat tgtttcacaa    720

tctgctgctg cttcaaatcc ttcgacaggt tcaggctcaa ctgctaccaa taactcaaac    780

tcgacttctt ctaactcaaa tgcctcaatt cataaggtcg ttaaaggaga tactctctgg    840

ggactttcgc aaaaatctgg cagcccaatt gcttcaatca aggcttggaa tcatttatct    900

agcgatacta ttttaattgg tcagtatcta cgaataaaat aa                       942
```

<210> SEQ ID NO 5
<211> LENGTH: 906
<212> TYPE: DNA
<213> ORGANISM: Artificial
<220> FEATURE:
<223> OTHER INFORMATION: Gene construct comprising signal peptide coding sequence, TNFalpha affinity domain coding sequence and surface attachment domain coding sequence.

<400> SEQUENCE: 5

```
atggctaaaa aaaagattat ctcagctatt ttaatgtcta cagtgatact ttctgctgca     60

gccccgttgt caggtgttta cgctcttgaa atctcatcat actgtgatgc tggatccgtt    120

gataacaaat ttaataaaga acttggttgg gctattggag aaatcggaac tcttccaaac    180

ttaaatcacc aacaattccg tgcttttatt ctttcacttt gggatgatcc atcacaatca    240

gctaaccttt tggctgaagc taaaaaactt aacgatgctc aagctccaaa agaattctct    300

ggaaccaata gcagttcaac tacttatacc gtcaaatctg gtgatactct ttggggaatc    360

tcacaaagat atggaattag tgtcgctcaa attcaaagtg cgaataatct taaaagtacc    420

attatctaca ttggtcaaaa acttgtactg acaggttcag cttcttctac aaattcaggt    480

ggttcaaaca attccgcaag cactactcca accacttctg tgacacctgc aaaaccaact    540

tcacaaacaa ctgttaaggt taaatccgga gatacccttt gggcgctatc agtaaaatat    600

aaaactagta ttgctcaatt gaaaagttgg aatcatttaa gttcagatac catttatatt    660

ggtcaaaatc ttattgtttc acaatctgct gctgcttcaa atccttcgac aggttcaggc    720

tcaactgcta ccaataactc aaactcgact tcttctaact caaatgcctc aattcataag    780

gtcgttaaag gagatactct ctggggactt tcgcaaaaat ctggcagccc aattgcttca    840

atcaaggctt ggaatcattt atctagcgat actattttaa ttggtcagta tctacgaata    900

aaataa                                                                906
```

<210> SEQ ID NO 6
<211> LENGTH: 176
<212> TYPE: PRT
<213> ORGANISM: Artificial
<220> FEATURE:
<223> OTHER INFORMATION: Protein construct comprising signal peptide, TNFalpha affinity domain and surface attachment domain.

<400> SEQUENCE: 6

```
Met Ala Lys Lys Lys Ile Ile Ser Ala Ile Leu Met Ser Thr Val Ile
1               5                   10                  15

Leu Ser Ala Ala Ala Pro Leu Ser Gly Val Tyr Ala Gly Ser Val Asp
            20                  25                  30

Asn Lys Phe Asn Lys Glu Leu Gly Trp Ala Ile Gly Glu Ile Gly Thr
        35                  40                  45

Leu Pro Asn Leu Asn His Gln Gln Phe Arg Ala Phe Ile Leu Ser Leu
    50                  55                  60

Trp Asp Asp Pro Ser Gln Ser Ala Asn Leu Leu Ala Glu Ala Lys Lys
65                  70                  75                  80

Leu Asn Asp Ala Gln Ala Pro Lys Glu Phe Phe Asp Gly Ala Ser Ser
                85                  90                  95

Ala Gly Asn Thr Asn Ser Gly Gly Ser Thr Thr Thr Ile Thr Asn Asn
            100                 105                 110

Asn Ser Gly Thr Asn Ser Ser Ser Thr Thr Tyr Thr Val Lys Ser Gly
        115                 120                 125

Asp Thr Leu Trp Gly Ile Ser Gln Arg Tyr Gly Ile Ser Val Ala Gln
    130                 135                 140

Ile Gln Ser Ala Asn Asn Leu Lys Ser Thr Ile Ile Tyr Ile Gly Gln
145                 150                 155                 160

Lys Leu Val Leu Thr Gly Ser Ala Ser Ser Thr Asn Ser Gly Gly Ser
                165                 170                 175
```

<210> SEQ ID NO 7
<211> LENGTH: 185
<212> TYPE: PRT
<213> ORGANISM: Artificial
<220> FEATURE:
<223> OTHER INFORMATION: Protein construct comprising signal peptide, TNFalpha affinity domain and surface attachment domain.

<400> SEQUENCE: 7

```
Met Ala Lys Lys Lys Ile Ile Ser Ala Ile Leu Met Ser Thr Val Ile
1               5                   10                  15

Leu Ser Ala Ala Ala Pro Leu Ser Gly Val Tyr Ala Leu Glu Ile Ser
            20                  25                  30

Ser Tyr Cys Asp Ala Gly Ser Val Asp Asn Lys Phe Asn Lys Glu Leu
        35                  40                  45

Gly Trp Ala Ile Gly Glu Ile Gly Thr Leu Pro Asn Leu Asn His Gln
    50                  55                  60

Gln Phe Arg Ala Phe Ile Leu Ser Leu Trp Asp Asp Pro Ser Gln Ser
65                  70                  75                  80

Ala Asn Leu Leu Ala Glu Ala Lys Lys Leu Asn Asp Ala Gln Ala Pro
                85                  90                  95

Lys Glu Phe Phe Asp Gly Ala Ser Ser Ala Gly Asn Thr Asn Ser Gly
            100                 105                 110

Gly Ser Thr Thr Thr Ile Thr Asn Asn Asn Ser Gly Thr Asn Ser Ser
        115                 120                 125

Ser Thr Thr Tyr Thr Val Lys Ser Gly Asp Thr Leu Trp Gly Ile Ser
    130                 135                 140

Gln Arg Tyr Gly Ile Ser Val Ala Gln Ile Gln Ser Ala Asn Asn Leu
145                 150                 155                 160

Lys Ser Thr Ile Ile Tyr Ile Gly Gln Lys Leu Val Leu Thr Gly Ser
                165                 170                 175

Ala Ser Ser Thr Asn Ser Gly Gly Ser
            180                 185
```

<210> SEQ ID NO 8
<211> LENGTH: 324
<212> TYPE: PRT
<213> ORGANISM: Artificial
<220> FEATURE:
<223> OTHER INFORMATION: Protein construct comprising signal peptide, TNFalpha affinity domain and surface attachment domain.

<400> SEQUENCE: 8

```
Met Ala Lys Lys Lys Ile Ile Ser Ala Ile Leu Met Ser Thr Val Ile
1               5                   10                  15

Leu Ser Ala Ala Ala Pro Leu Ser Gly Val Tyr Ala Leu Glu Ile Ser
            20                  25                  30

Ser Tyr Cys Asp Ala Gly Ser Val Asp Asn Lys Phe Asn Lys Glu Leu
        35                  40                  45

Gly Trp Ala Ile Gly Glu Ile Gly Thr Leu Pro Asn Leu Asn His Gln
    50                  55                  60

Gln Phe Arg Ala Phe Ile Leu Ser Leu Trp Asp Asp Pro Ser Gln Ser
65                  70                  75                  80

Ala Asn Leu Leu Ala Glu Ala Lys Lys Leu Asn Asp Ala Gln Ala Pro
                85                  90                  95

Lys Glu Phe Phe Asp Gly Ala Ser Ser Ala Gly Asn Thr Asn Ser Gly
            100                 105                 110

Gly Ser Thr Thr Thr Ile Thr Asn Asn Asn Ser Gly Thr Asn Ser Ser
        115                 120                 125
```

```
Ser Thr Thr Tyr Thr Val Lys Ser Gly Asp Thr Leu Trp Gly Ile Ser
    130                 135                 140

Gln Arg Tyr Gly Ile Ser Val Ala Gln Ile Gln Ser Ala Asn Asn Leu
145                 150                 155                 160

Lys Ser Thr Ile Ile Tyr Ile Gly Gln Lys Leu Val Leu Thr Gly Ser
                165                 170                 175

Ala Ser Ser Thr Asn Ser Gly Gly Ser Asn Asn Ser Ala Ser Thr Thr
            180                 185                 190

Pro Thr Thr Ser Val Thr Pro Ala Lys Pro Thr Ser Gln Thr Thr Val
        195                 200                 205

Lys Val Lys Ser Gly Asp Thr Leu Trp Ala Leu Ser Val Lys Tyr Lys
    210                 215                 220

Thr Ser Ile Ala Gln Leu Lys Ser Trp Asn His Leu Ser Ser Asp Thr
225                 230                 235                 240

Ile Tyr Ile Gly Gln Asn Leu Ile Val Ser Gln Ser Ala Ala Ala Ser
                245                 250                 255

Asn Pro Ser Thr Gly Ser Gly Ser Thr Ala Thr Asn Asn Ser Asn Ser
            260                 265                 270

Thr Ser Ser Asn Ser Asn Ala Ser Ile His Lys Val Val Lys Gly Asp
        275                 280                 285

Thr Leu Trp Gly Leu Ser Gln Lys Ser Gly Ser Pro Ile Ala Ser Ile
    290                 295                 300

Lys Ala Trp Asn His Leu Ser Ser Asp Thr Ile Leu Ile Gly Gln Tyr
305                 310                 315                 320

Leu Arg Ile Lys


<210> SEQ ID NO 9
<211> LENGTH: 313
<212> TYPE: PRT
<213> ORGANISM: Artificial
<220> FEATURE:
<223> OTHER INFORMATION: Protein construct comprising signal peptide,
      TNFalpha affinity domain and surface attachment domain.

<400> SEQUENCE: 9

Met Ala Lys Lys Lys Ile Ile Ser Ala Ile Leu Met Ser Thr Val Ile
1               5                   10                  15

Leu Ser Ala Ala Ala Pro Leu Ser Gly Val Tyr Ala Leu Glu Ile Ser
            20                  25                  30

Ser Tyr Cys Asp Ala Gly Ser Val Asp Asn Lys Phe Asn Lys Glu Leu
        35                  40                  45

Gly Trp Ala Ile Gly Glu Ile Gly Thr Leu Pro Asn Leu Asn His Gln
    50                  55                  60

Gln Phe Arg Ala Phe Ile Leu Ser Leu Trp Asp Asp Pro Ser Gln Ser
65                  70                  75                  80

Ala Asn Leu Leu Ala Glu Ala Lys Lys Leu Asn Asp Ala Gln Ala Pro
                85                  90                  95

Lys Glu Phe Ser Gly Gly Ser Thr Thr Thr Ile Thr Asn Asn Asn Ser
            100                 105                 110

Gly Thr Asn Ser Ser Ser Thr Thr Tyr Thr Val Lys Ser Gly Asp Thr
        115                 120                 125

Leu Trp Gly Ile Ser Gln Arg Tyr Gly Ile Ser Val Ala Gln Ile Gln
    130                 135                 140

Ser Ala Asn Asn Leu Lys Ser Thr Ile Ile Tyr Ile Gly Gln Lys Leu
145                 150                 155                 160
```

```
Val Leu Thr Gly Ser Ala Ser Ser Thr Asn Ser Gly Gly Ser Asn Asn
                165                 170                 175

Ser Ala Ser Thr Thr Pro Thr Thr Ser Val Thr Pro Ala Lys Pro Thr
            180                 185                 190

Ser Gln Thr Thr Val Lys Val Lys Ser Gly Asp Thr Leu Trp Ala Leu
        195                 200                 205

Ser Val Lys Tyr Lys Thr Ser Ile Ala Gln Leu Lys Ser Trp Asn His
    210                 215                 220

Leu Ser Ser Asp Thr Ile Tyr Ile Gly Gln Asn Leu Ile Val Ser Gln
225                 230                 235                 240

Ser Ala Ala Ala Ser Asn Pro Ser Thr Gly Ser Gly Ser Thr Ala Thr
                245                 250                 255

Asn Asn Ser Asn Ser Thr Ser Ser Asn Ser Asn Ala Ser Ile His Lys
            260                 265                 270

Val Val Lys Gly Asp Thr Leu Trp Gly Leu Ser Gln Lys Ser Gly Ser
        275                 280                 285

Pro Ile Ala Ser Ile Lys Ala Trp Asn His Leu Ser Ser Asp Thr Ile
    290                 295                 300

Leu Ile Gly Gln Tyr Leu Arg Ile Lys
305                 310


<210> SEQ ID NO 10
<211> LENGTH: 301
<212> TYPE: PRT
<213> ORGANISM: Artificial
<220> FEATURE:
<223> OTHER INFORMATION: Protein construct comprising signal peptide,
      TNFalpha affinity domain and surface attachment domain.

<400> SEQUENCE: 10

Met Ala Lys Lys Lys Ile Ile Ser Ala Ile Leu Met Ser Thr Val Ile
1               5                   10                  15

Leu Ser Ala Ala Ala Pro Leu Ser Gly Val Tyr Ala Leu Glu Ile Ser
            20                  25                  30

Ser Tyr Cys Asp Ala Gly Ser Val Asp Asn Lys Phe Asn Lys Glu Leu
        35                  40                  45

Gly Trp Ala Ile Gly Glu Ile Gly Thr Leu Pro Asn Leu Asn His Gln
    50                  55                  60

Gln Phe Arg Ala Phe Ile Leu Ser Leu Trp Asp Asp Pro Ser Gln Ser
65                  70                  75                  80

Ala Asn Leu Leu Ala Glu Ala Lys Lys Leu Asn Asp Ala Gln Ala Pro
                85                  90                  95

Lys Glu Phe Ser Gly Thr Asn Ser Ser Ser Thr Thr Tyr Thr Val Lys
            100                 105                 110

Ser Gly Asp Thr Leu Trp Gly Ile Ser Gln Arg Tyr Gly Ile Ser Val
        115                 120                 125

Ala Gln Ile Gln Ser Ala Asn Asn Leu Lys Ser Thr Ile Ile Tyr Ile
    130                 135                 140

Gly Gln Lys Leu Val Leu Thr Gly Ser Ala Ser Ser Thr Asn Ser Gly
145                 150                 155                 160

Gly Ser Asn Asn Ser Ala Ser Thr Thr Pro Thr Thr Ser Val Thr Pro
                165                 170                 175

Ala Lys Pro Thr Ser Gln Thr Thr Val Lys Val Lys Ser Gly Asp Thr
            180                 185                 190

Leu Trp Ala Leu Ser Val Lys Tyr Lys Thr Ser Ile Ala Gln Leu Lys
        195                 200                 205
```

```
Ser Trp Asn His Leu Ser Ser Asp Thr Ile Tyr Ile Gly Gln Asn Leu
    210                 215                 220

Ile Val Ser Gln Ser Ala Ala Ala Ser Asn Pro Ser Thr Gly Ser Gly
225                 230                 235                 240

Ser Thr Ala Thr Asn Asn Ser Asn Ser Thr Ser Ser Asn Ser Asn Ala
                245                 250                 255

Ser Ile His Lys Val Val Lys Gly Asp Thr Leu Trp Gly Leu Ser Gln
            260                 265                 270

Lys Ser Gly Ser Pro Ile Ala Ser Ile Lys Ala Trp Asn His Leu Ser
        275                 280                 285

Ser Asp Thr Ile Leu Ile Gly Gln Tyr Leu Arg Ile Lys
    290                 295                 300


<210> SEQ ID NO 11
<211> LENGTH: 437
<212> TYPE: PRT
<213> ORGANISM: Lactococcus lactis
<220> FEATURE:
<223> OTHER INFORMATION: AcmA protein

<400> SEQUENCE: 11

Met Pro Val Ser Arg Val Lys Val Lys Asn Arg His Leu Lys Lys Lys
1               5                   10                  15

Thr Lys Lys Pro Leu Ala Phe Tyr Lys Pro Ala Thr Lys Phe Ala Gly
            20                  25                  30

Ala Val Leu Ile Ala Gly Thr Leu Thr Thr Thr His Glu Leu Leu Leu
        35                  40                  45

Gln Gln Thr Ser Pro Met Val Gln Ala Ala Thr Asn Ser Ser Glu Val
    50                  55                  60

Phe Ile Glu Ser Ile Ala Ala Ser Ala Lys Pro Val Ala Asp Ala Asn
65                  70                  75                  80

Gly Leu Tyr Pro Ser Val Met Ile Ala Gln Ala Ile Leu Glu Ser Asn
                85                  90                  95

Trp Gly Ser Ser Gln Leu Ser Arg Ala Pro Tyr Tyr Asn Leu Phe Gly
            100                 105                 110

Ile Gln Gly Thr Tyr Gln Gly Lys Ser Val Val Phe Lys Thr Gln Glu
        115                 120                 125

Tyr Leu Asn Gly Lys Trp Val Thr Lys Asp Met Pro Phe Arg Val Tyr
    130                 135                 140

Pro Ser Phe Asn Gln Ser Phe Gln Asp Asn Ala Tyr Val Leu Lys Thr
145                 150                 155                 160

Thr Asn Phe Gly Asn Gly Pro Tyr Tyr Ala Lys Ala Trp Arg Ala Asn
                165                 170                 175

Ala Ala Thr Tyr Gln Asp Ala Thr Ala Ala Leu Thr Gly Arg Tyr Ala
            180                 185                 190

Thr Asp Pro Ser Tyr Gly Ala Ser Leu Asn Arg Ile Ile Ser Gln Tyr
        195                 200                 205

Asn Leu Thr Arg Phe Asp Gly Ala Ser Ser Ala Gly Asn Thr Asn Ser
    210                 215                 220

Gly Gly Ser Thr Thr Thr Ile Thr Asn Asn Asn Ser Gly Thr Asn Ser
225                 230                 235                 240

Ser Ser Thr Thr Tyr Thr Val Lys Ser Gly Asp Thr Leu Trp Gly Ile
                245                 250                 255

Ser Gln Arg Tyr Gly Ile Ser Val Ala Gln Ile Gln Ser Ala Asn Asn
            260                 265                 270
```

Leu Lys Ser Thr Ile Ile Tyr Ile Gly Gln Lys Leu Val Leu Thr Gly
        275                 280                 285

Ser Ala Ser Ser Thr Asn Ser Gly Gly Ser Asn Asn Ser Ala Ser Thr
    290                 295                 300

Thr Pro Thr Thr Ser Val Thr Pro Ala Lys Pro Thr Ser Gln Thr Thr
305                 310                 315                 320

Val Lys Val Lys Ser Gly Asp Thr Leu Trp Ala Leu Ser Val Lys Tyr
                325                 330                 335

Lys Thr Ser Ile Ala Gln Leu Lys Ser Trp Asn His Leu Ser Ser Asp
            340                 345                 350

Thr Ile Tyr Ile Gly Gln Asn Leu Ile Val Ser Gln Ser Ala Ala Ala
        355                 360                 365

Ser Asn Pro Ser Thr Gly Ser Gly Ser Thr Ala Thr Asn Asn Ser Asn
    370                 375                 380

Ser Thr Ser Ser Asn Ser Asn Ala Ser Ile His Lys Val Val Lys Gly
385                 390                 395                 400

Asp Thr Leu Trp Gly Leu Ser Gln Lys Ser Gly Ser Pro Ile Ala Ser
                405                 410                 415

Ile Lys Ala Trp Asn His Leu Ser Ser Asp Thr Ile Leu Ile Gly Gln
            420                 425                 430

Tyr Leu Arg Ile Lys
        435

<210> SEQ ID NO 12
<211> LENGTH: 461
<212> TYPE: PRT
<213> ORGANISM: Lactococcus lactis
<220> FEATURE:
<223> OTHER INFORMATION: Usp45 protein

<400> SEQUENCE: 12

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Asp Thr Asn Ser Asp
            20                  25                  30

Ile Ala Lys Gln Asp Ala Thr Ile Ser Ser Ala Gln Ser Ala Lys Ala
        35                  40                  45

Gln Ala Gln Ala Gln Val Asp Ser Leu Gln Ser Lys Val Asp Ser Leu
    50                  55                  60

Gln Gln Lys Gln Thr Ser Thr Lys Ala Gln Ile Ala Lys Ile Glu Ser
65                  70                  75                  80

Glu Ala Lys Ala Leu Asn Ala Gln Ile Ala Thr Leu Asn Glu Ser Ile
                85                  90                  95

Lys Glu Arg Thr Lys Thr Leu Glu Ala Gln Ala Arg Ser Ala Gln Val
            100                 105                 110

Asn Ser Ser Ala Thr Asn Tyr Met Asp Ala Val Val Asn Ser Lys Ser
        115                 120                 125

Leu Thr Asp Val Ile Gln Lys Val Thr Ala Ile Ala Thr Val Ser Ser
    130                 135                 140

Ala Asn Lys Gln Met Leu Glu Gln Gln Glu Lys Glu Gln Lys Glu Leu
145                 150                 155                 160

Ser Gln Lys Ser Glu Thr Val Lys Lys Asn Tyr Asn Gln Phe Val Ser
                165                 170                 175

Leu Ser Gln Ser Leu Asp Ser Gln Ala Gln Glu Leu Thr Ser Gln Gln
            180                 185                 190

```
Ala Glu Leu Lys Val Ala Thr Leu Asn Tyr Gln Ala Thr Ile Ala Thr
        195                 200                 205

Ala Gln Asp Lys Lys Gln Ala Leu Leu Asp Glu Lys Ala Ala Ala Glu
    210                 215                 220

Lys Ala Ala Gln Glu Ala Ala Lys Lys Gln Ala Ala Tyr Glu Ala Gln
225                 230                 235                 240

Gln Lys Glu Ala Ala Gln Ala Gln Ala Ala Ser Thr Ala Ala Thr Ala
                245                 250                 255

Lys Ala Val Glu Ala Ala Thr Ser Ser Ala Ser Ala Ser Ser Ser Gln
            260                 265                 270

Ala Pro Gln Val Ser Thr Ser Thr Asp Asn Thr Thr Ser Asn Ala Ser
        275                 280                 285

Ala Ser Asn Ser Ser Asn Ser Ser Ser Asn Ser Ser Ser Ser Ser Ser
    290                 295                 300

Ser Ser Ser Ser Ser Ser Ser Ser Ser Ser Asn Ser Asn Ala Gly Gly
305                 310                 315                 320

Asn Thr Asn Ser Gly Thr Ser Thr Gly Asn Thr Gly Gly Thr Thr Thr
                325                 330                 335

Gly Gly Ser Gly Ile Asn Ser Ser Pro Ile Gly Asn Pro Tyr Ala Gly
            340                 345                 350

Gly Gly Cys Thr Asp Tyr Val Trp Gln Tyr Phe Ala Ala Gln Gly Ile
        355                 360                 365

Tyr Ile Arg Asn Ile Met Pro Gly Asn Gly Gly Gln Trp Ala Ser Asn
    370                 375                 380

Gly Pro Ala Gln Gly Val Leu His Val Val Gly Ala Ala Pro Gly Val
385                 390                 395                 400

Ile Ala Ser Ser Phe Ser Ala Asp Phe Val Gly Tyr Ala Asn Ser Pro
                405                 410                 415

Tyr Gly His Val Ala Ile Val Lys Ser Val Asn Ser Asp Gly Thr Ile
            420                 425                 430

Thr Ile Lys Glu Gly Gly Tyr Gly Thr Thr Trp Trp Gly His Glu Arg
        435                 440                 445

Thr Val Ser Ala Ser Gly Val Thr Phe Leu Met Pro Asn
    450                 455                 460


<210> SEQ ID NO 13
<211> LENGTH: 9
<212> TYPE: PRT
<213> ORGANISM: Artificial Sequence
<220> FEATURE:
<223> OTHER INFORMATION: Synthetic pro-peptide

<400> SEQUENCE: 13

Leu Glu Ile Ser Ser Tyr Cys Asp Ala
1               5


<210> SEQ ID NO 14
<211> LENGTH: 9
<212> TYPE: PRT
<213> ORGANISM: Artificial Sequence
<220> FEATURE:
<223> OTHER INFORMATION: Synthetic pro-peptide

<400> SEQUENCE: 14

Leu Glu Ile Ser Ser Thr Cys Asp Ala
1               5
```

<210> SEQ ID NO 15
<211> LENGTH: 9
<212> TYPE: PRT
<213> ORGANISM: Artificial Sequence
<220> FEATURE:
<223> OTHER INFORMATION: Synthetic pro-peptide

<400> SEQUENCE: 15

Leu Gln Val Asp Asp Ile Pro Ser Ala
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic pro-peptide

<400> SEQUENCE: 16

Leu Gly Ile Ser Ser Thr Cys Asn Ala
1               5

<210> SEQ ID NO 17
<211> LENGTH: 8
<212> TYPE: PRT
<213> ORGANISM: Artificial Sequence
<220> FEATURE:
<223> OTHER INFORMATION: LysM Repeat
<220> FEATURE:
<221> NAME/KEY: misc_feature
<222> LOCATION: (1)..(1)
<223> OTHER INFORMATION: Xaa = Tyr or Val
<220> FEATURE:
<221> NAME/KEY: misc_feature
<222> LOCATION: (2)..(2)
<223> OTHER INFORMATION: Xaa = 0 to 4 residues of any naturally occurring amino acid
<220> FEATURE:
<221> NAME/KEY: misc_feature
<222> LOCATION: (5)..(5)
<223> OTHER INFORMATION: Xaa = Ser or Thr
<220> FEATURE:
<221> NAME/KEY: misc_feature
<222> LOCATION: (6)..(6)
<223> OTHER INFORMATION: Xaa = Val, Leu, Ile, or Ala
<220> FEATURE:
<221> NAME/KEY: misc_feature
<222> LOCATION: (7)..(7)
<223> OTHER INFORMATION: X = 0 to 2 residues of any naturally occurring amino acid
<220> FEATURE:
<221> NAME/KEY: misc_feature
<222> LOCATION: (8)..(8)
<223> OTHER INFORMATION: Xaa = Val, Leu, Ile, or Ala

<400> SEQUENCE: 17

Xaa Xaa Gly Asp Xaa Xaa Xaa Xaa
1               5

<210> SEQ ID NO 18
<211> LENGTH: 8
<212> TYPE: PRT
<213> ORGANISM: Artificial Sequence
<220> FEATURE:
<223> OTHER INFORMATION: CBD consensus sequence
<220> FEATURE:
<221> NAME/KEY: misc_feature
<222> LOCATION: (2)..(2)
<223> OTHER INFORMATION: Xaa = 0 to 5 residues of any naturally occurring amino acid
<220> FEATURE:
<221> NAME/KEY: misc_feature
<222> LOCATION: (4)..(4)
<223> OTHER INFORMATION: Xaa = any naturally occurring amino acid
<220> FEATURE:
<221> NAME/KEY: misc_feature
<222> LOCATION: (5)..(6)
<223> OTHER INFORMATION: Xaa = Trp, Tyr, or Ile
<220> FEATURE:
<221> NAME/KEY: misc_feature
<222> LOCATION: (7)..(7)
<223> OTHER INFORMATION: Xaa = Tyr, Val, or Leu
<220> FEATURE:
<221> NAME/KEY: misc_feature
<222> LOCATION: (8)..(8)
<223> OTHER INFORMATION: Xaa = Phe or Val

<400> SEQUENCE: 18

Gly Xaa Gly Xaa Xaa Xaa Xaa Xaa
1               5

<210> SEQ ID NO 19
<211> LENGTH: 8
<212> TYPE: PRT
<213> ORGANISM: Artificial Sequence
<220> FEATURE:
<223> OTHER INFORMATION: Lipobox
<220> FEATURE:
<221> NAME/KEY: misc_feature
<222> LOCATION: (2)..(2)
<223> OTHER INFORMATION: Xaa = 1 to 10 residues of any naturally occurring amino acid
<220> FEATURE:
<221> NAME/KEY: misc_feature
<222> LOCATION: (3)..(3)
<223> OTHER INFORMATION: Xaa = any naturally occurring amino acid other than Asp, Glu, Arg, Lys
<220> FEATURE:
<221> NAME/KEY: misc_feature
<222> LOCATION: (4)..(4)
<223> OTHER INFORMATION: Xaa = 7 to 17 naturally occurring amino acid residues other than Asp, Glu, Arg, Lys
<220> FEATURE:
<221> NAME/KEY: misc_feature
<222> LOCATION: (5)..(5)
<223> OTHER INFORMATION: Xaa = Leu, Val, Thr, Ile, Met, or Gly
<220> FEATURE:
<221> NAME/KEY: misc_feature
<222> LOCATION: (6)..(6)
<223> OTHER INFORMATION: Xaa = Asp, Ser, Thr, Ile, Al, Gly, Met, Leu, Cys, Pro, Phe, or Leu
<220> FEATURE:
<221> NAME/KEY: misc_feature
<222> LOCATION: (7)..(7)
<223> OTHER INFORMATION: Xaa = Asp, Gly, Leu, Ile, Ser, Val, Thr, Phe, or Pro

<400> SEQUENCE: 19

Met Xaa Xaa Xaa Xaa Xaa Xaa Cys
1               5

<210> SEQ ID NO 20
<211> LENGTH: 5
<212> TYPE: PRT
<213> ORGANISM: Artificial Sequence
<220> FEATURE:
<223> OTHER INFORMATION: LPxTG consensus sequence
<220> FEATURE:
<221> NAME/KEY: misc_feature
<222> LOCATION: (3)..(3)
<223> OTHER INFORMATION: Xaa = any naturally occurring amino acid

<400> SEQUENCE: 20

Leu Pro Xaa Thr Gly
1               5

-continued

```
<210> SEQ ID NO 21
<211> LENGTH: 28
<212> TYPE: PRT
<213> ORGANISM: Artificial Sequence
<220> FEATURE:
<223> OTHER INFORMATION: Secretion signal sequence

<400> SEQUENCE: 21

Met Ala Lys Lys Lys Ile Ile Ser Ala Ile Leu Met Ser Thr Val Ile
1               5                   10                  15

Leu Ser Ala Ala Ala Pro Leu Ser Gly Val Tyr Ala
            20                  25


<210> SEQ ID NO 22
<211> LENGTH: 58
<212> TYPE: PRT
<213> ORGANISM: Artificial Sequence
<220> FEATURE:
<223> OTHER INFORMATION: affibody sequence Z00185

<400> SEQUENCE: 22

Val Asp Asn Lys Phe Asn Lys Glu Leu Gly Trp Ala Ile Gly Glu Ile
1               5                   10                  15

Gly Thr Leu Pro Asn Leu Asn His Gln Gln Phe Arg Ala Phe Ile Leu
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55
```

MODIFIED FOOD GRADE MICROORGANISM FOR TREATMENT OF INFLAMMATORY BOWEL DISEASE

This application is a national phase of International Application No. PCT/EP2011/000019 filed Jan. 5, 2011 and published in the English language, which claims priority to EP 10000074.4 filed Jan. 7, 2010.

FIELD OF THE INVENTION

The present invention relates to microorganisms that have attached on their surface a TNFα binding polypeptide. Peptides attached to the surface of the microorganism are more resistant to chemical and enzymatic degradation in the gastrointestinal tract than are secreted proteins. Microorganisms of the invention are capable of binding TNFα in the gastrointestinal tract and therefore reduce the content of free TNFα and alleviate its pro-inflammatory effects in the gut. Microorganisms of the invention can be used as medicament in the treatment of inflammatory bowel disease.

BACKGROUND

Inflammatory bowel disease (IBD) refers to a group of gastrointestinal disorders characterized by chronic, relapsing inflammatory disorders of the gastrointestinal tract. Crohn's disease and ulcerative colitis are the two main subtypes of IBD.

The etiology of IBD is unclear. IBD appears as multifactorial disease, with genetic and environmental factors probably cooperating in their development.

Patients typically suffer from frequent and chronically relapsing flares, resulting in diarrhea, abdominal pain, rectal bleeding and malnutrition. Crohn's disease can be distinguished from ulcerative colitis in that the inflammation associated with Crohn's disease is transmural and often discontinuous. By contrast, the inflammatory changes of ulcerative colitis typically involve only the superficial mucosal and submucosal layers of the intestinal wall. Crohn's disease most commonly involves the ileum and colon but can affect any region of the gut; ulcerative colitis always involves the rectum, and inflammation may extend as far as the caecum in a continuous pattern. Patients with IBD often have various extra-intestinal symptoms such as arthalgias, and are more likely to have other chronic inflammatory diseases, particularly primary sclerosing cholangitis, ankylosing spondylitis and psoriasis. Etiology, genetics and pathogenesis of IBD is described by Hugot (1999) and Cho (2008).

Since the etiology of both diseases is undetermined the causal therapy does not exist. The most commonly used conventional therapies are anti-inflammatory medicaments such as corticosteroids, salicilates, and immunosuppressives such as cyclosporine, mercaptopurine and azathioprine. Recently, biologic therapies have received a great amount of attention.

The mucosal immune system is the central effector of intestinal inflammation and injury, with cytokines playing a central role in modulating inflammation. Cytokines may, therefore, be a logical target for IBD therapy using specific cytokine inhibitors. In this context compounds described by Schwartz M (2008) blocking the effect of tumor necrosis factor α (TNFα) or its receptor are of interest.

TNFα is a cytokine produced by numerous cell types, including monocytes and macrophages, and was originally identified on the base its ability to induce the necrosis of certain mouse tumors as described by Old (1985). TNFα has been implicated in the pathophysiology of a variety of other human diseases and disorders, including sepsis, infections, autoimmune diseases, transplant rejection and graft-versus-host disease. TNFα promotes the inflammatory response, which, in turn, causes many of the clinical problems associated with autoimmune disorders such as rheumatoid arthritis, ankylosing spondylitis, Crohn's disease, psoriasis and refractory asthma. These disorders are sometimes treated by using a TNFα inhibitor or by counteracting TNFα activity.

In particular, monoclonal antibodies against TNFα are routinely used in parenteral therapy of IBD as described by Sandborn (1999). Commercially available are infliximab, adalimumab and certolizumab pegol. Since antibodies are administered mainly by subcutaneous injection, serious unwanted effects emerge such as headache, abscess, upper respiratory tract infection and fatigue.

De Silva (1992) reported on abundant presence of TNFα in the stool of IBD patients. Local delivery on the place of inflammation could solve unwanted effects associated with systemic delivery. This was achieved by Worledge (2000), with successful treatment of experimental colitis in rats by orally administering avian IgY anti TNFα antibodies with the capability of deactivating/removing TNFα.

Antibodies and antibody related derivatives against TNFα are not always the optimal choice. The high cost of production of these immunoglobulin preparations prohibits their large-scale application. Antibodies, like other protein molecules, are not stable in the gastrointestinal tract.

The use of genetically engineered bacteria that produce and deliver compounds that block the activity of TNFα could provide a solution. In this respect, lactic acid bacteria, which are normal commensals of the gut and other mucosal surfaces of human and animals and generally regarded as safe, represent ideal candidates.

WO2007/025977 discloses delivery of secreted antibodies against TNFα, and of fragments of such antibodies (so-called nanobodies), to the intestine for the treatment of enterocolitis using genetically engineered microorganisms such as lactic acid bacteria. The secreted antibodies of WO2007/025977 do not include a surface attachment domain, and are thus not attached to the cell's surface and more prone to chemical and biological degradation in the gut.

WO97/14806 discloses a delivery system of biologically active compounds in the intestine, wherein non-invasive bacteria such as lactic acid bacteria are used to deliver biological active polypeptides to the gut. WO00/23471 discloses recombinant lactic acid bacteria that can be used to deliver IL-10 and soluble TNF receptor via oral route to the ileum to treat IBD. No attachment of the polypeptides to the surface of the microorganism is disclosed. Hence, the polypeptides are subject to rapid degradation. WO97/14806 uses the Usp45 secretion domain to ensure efficient secretion of the proteins.

EP1477802 discloses vaccines against infection with *Streptococcus pneunoniae*. The vaccine comprises the antigenic part of pneumococcal proteins (PpmA, SlrA), which are fused with a cell wall anchoring domain derived from the AcmA protein. The pneumococcal proteins of EP 1477802, however, do not comprise a TNFα binding domain, hence do not exhibit the therapeutic effects of the present microorganisms.

Hence it is known to produce peptides by lactic acid bacteria and secrete them into the gastrointestinal tract. Such peptides then generally undergo fast degradation.

SUMMARY OF THE INVENTION

The present invention addresses these problems by producing genetically modified microorganisms that have attached to their surface, or express on their surface, a TNFα binding polypeptide. Surface expression of TNFα binding polypeptides, or attachment of TNFα binding polypeptides, on lactic acid bacteria provides protection from chemical and enzymatic factors in the gastrointestinal tract. Such peptides are markedly more acid resistant. TNFα binding polypeptide expressed on the surface of mentioned microorganism may be TNFα binding Z domain (affibody). The peptide has stable and robust structure due to Z domain and is able to bind TNFα in the sample, for example body fluid.

The present invention thus relates to a gene construct coding for a polypeptide comprising a secretion signal peptide, a TNFα binding domain and surface attachment domain, said TNFα binding domain and said surface attachment domain being preferably separated by a spacer region, said gene construct preferably being under the control of a suitable promoter.

In a preferred embodiment of the invention, said secretion signal peptide is a signal peptide of Usp45 or its homologue.

In another preferred embodiment of the invention, said secretion signal peptide is adjacent a peptide sequence selected from LEISSYCDA (SEQ ID No: 13), LEISSTCDA (SEQ ID No: 14), LQVDDIPSA (SEQ ID No: 15) or LGISSTCNA (SEQ ID No: 16), or homologues thereof.

In another preferred embodiment of the invention, said surface attachment domain comprises at least 10, or at least 20 consecutive amino acid residues of the C terminal part of AcmA, or of homologues of the AcmA protein. In one embodiment, the at least 10, or at least 20 consecutive amino acid residues include the last (C-terminal) amino acid residue of the C terminal part of the AcmA protein, or of homologues of the AcmA protein. In another embodiment, the consecutive amino acid residues are in the C-terminal half, preferably in the C-terminal third, of the AcmA protein, or of homologues of the AcmA protein.

In another preferred embodiment of the invention, said surface attachment domain comprises 1 to 12, preferably 1 to 6, more preferably 2 to 4, or most preferred 3 LysM repeats.

In another preferred embodiment of the invention, said spacer region comprises at least 3, 5, 10, 20, or 40 consecutive amino acids of the AcmA protein, or of homologues of the AcmA protein.

In another preferred embodiment of the invention, the length of spacer region is 5 to 50 amino acids, preferably 10 to 30, more preferably 15-25, most preferably 20 amino acids.

In another preferred embodiment of the invention, said construct is coding for a protein sequence (a) of any one of SEQ ID NO:6 to SEQ ID NO:10, or (b) for a protein sequence which is at least 50, 80, 90, 95, 98, or 99% identical to any one of said sequences under (a), and conferring the same biological function as the said sequence under (a).

The invention further relates to a protein construct encoded by a gene construct of any one of the above claims.

The invention also relates to a microorganism, preferably a GRAS microorganism, having attached to its surface a protein comprising a TNFα binding domain. In a preferred embodiment, said attachment to said surface is a non-covalent attachment. The attachment, however, can also be covalent attachment.

In a preferred embodiment, said attachment to said surface is by at least one protein domain of said protein, said protein domain being selected from the group consisting of LysM repeat, choline binding domain, lipobox and LPxTG motif. The LysM repeat domain is preferred.

In a preferred embodiment, said protein comprising a TNFα binding domain is a protein construct as defined above. Hence, said protein comprising a TNFα binding domain may have a sequence (a) of any one of SEQ ID NO:6 to SEQ ID NO:10, or (b) a sequence which are at least 80% identical to any one of said sequences under (a), and preferably conferring the same biological function as said sequence under (a).

In a preferred embodiment, said microorganism is genetically modified to express said protein comprising a TNFα binding domain on its surface. This shall include microorganisms that express the protein, secrete the protein into the medium, wherein said protein is thereafter attached to the surface of said microorganism.

The invention further relates to a genetically modified microorganism preferably produced from a GRAS microorganism, said genetically modified microorganism expressing on its surface a protein comprising a TNFα binding domain.

In a preferred embodiment of the invention, microorganisms of the invention are lactic acid bacterium, *Lactococcus lactis*, or *Lactococcus* spec.

In another preferred embodiment of the invention, the microorganism of the invention comprises a gene construct as defined above.

In another preferred embodiment of the invention, the microorganism of the invention comprises a protein construct as defined above.

The invention also relates to a method for producing a genetically modified microorganism as described above, said method comprising introducing of a the above gene construct into a GRAS microorganism.

In a preferred embodiment of the invention, said gene construct is in a plasmid vector capable of replicating in said microorganism, or said gene construct is integrated into the genome of said microorganism.

The invention further relates to a genetically modified microorganism as described above for use as a medicament.

The invention further relates to the above microorganism for the treatment of inflammatory bowel disease, chronic colitis, Crohn's disease or ulcerative colitis.

The invention further relates to the above microorganism for reducing the content of free TNFα in the gastrointestinal tract of a subject.

The invention further relates to a pharmaceutical composition comprising a modified microorganism as described above. The pharmaceutical composition is preferably for oral administration, for example a tablet, or a capsule, preferably an enteric-coated tablet or capsule. The pharmaceutical preparation may also be in form of a suppository. The microorganism in the pharmaceutical composition can be viable or non-viable. In one embodiment the microorganism is non-viable.

In a preferred embodiment said pharmaceutical composition is adapted for oral administration.

The invention also relates to a food composition comprising the microorganism above.

In a preferred embodiment the food composition is selected from the group consisting of milk, yogurt, curd, cheese, fermented milks, milk based fermented products, ice cream, fermented cereal products, and milk based powders.

BRIEF DESCRIPTION OF THE FIGURES

FIGS. 7*a* and 7*b* shows sequence domains of peptides of the invention, and of known peptides AcmA and Usp45.

DETAILED DESCRIPTION OF THE INVENTION

Figure 1:
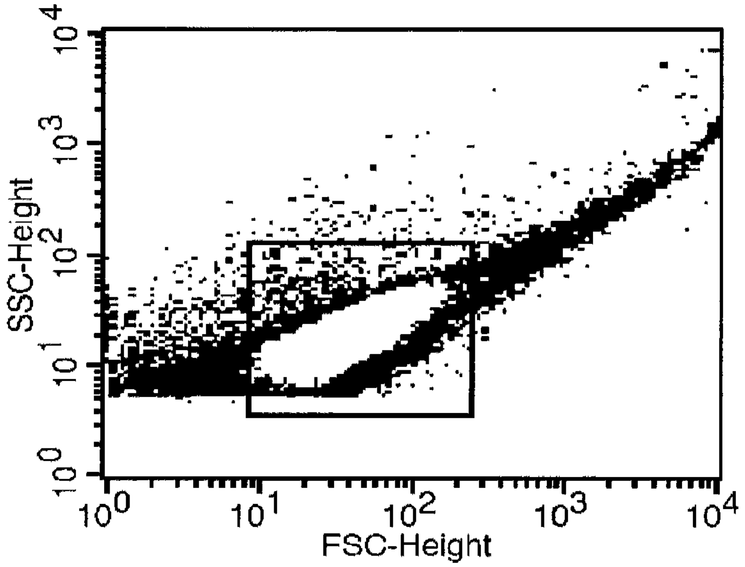
FIG. 1 shows a FSC-SSC density plot of bacterial cells.

The present invention relates to genetically modified GRAS (e.g., food grade) microorganisms that express, or have attached, a TNFα binding domain on their surface. Peptides expressed on the surface of microorganisms are more resistant to degradation in the gastrointestinal tract. Such microorganisms are capable of binding TNFα and therefore reducing the content of free (non-bound) TNFα and alleviating its pro-inflammatory effects in the gut. Such microorganisms can be used as medicament, e.g., in the treatment of IBD.

A TNFα binding domain may comprise antibodies or antibody fragments with ability to bind TNFα. The term "antibodies" refers to monoclonal antibodies, chimeric antibodies, humanized and fully human antibodies. "Antibody fragments" means a portion of an intact antibody, preferably the antigen binding or variable region of the intact antibody. Examples of antibody fragments include Fab, Fab', F(ab)' 1 and Fv fragments, diabodies, linear antibodies, single chain antibody molecules and multispecific antibodies formed from antibody fragments, and nanobodies.

A TNFα binding domain may also be an affibody, as disclosed in WO2006/092338. Affibody molecules are small and robust high affinity protein molecules that can be engineered to bind specifically to a large number of target proteins. The scaffold used for construction of affibodies is Z domain, an engineered version of B domain, which is one of the five stable three-alpha-helix bundle domains from the immunoglobulin binding region of staphylococcal protein A. Affibody molecules with unique binding properties are usually acquired by randomization of 13 amino acids located in two alpha-helices involved in the binding activity of the parent protein domain. Affibodies with affinity towards specific target protein are obtained by library construction and affinity selection.

A "TNFα binding domain", within the meaning of the present invention, shall thus be understood to be any peptide or domain to which TNFα binds, or which binds to TNFα. A TNFα binding domain can be a part of a larger protein, which then binds to TNFα, or to which TNFα binds. Preferred TNFα binding domains of the invention have a dissociation constant ($K_d$) with TNFα of less than 0.01, 0.1, 1, 10, 100, 1000 nM. With regard to the formation of a ligand-protein complex (C) from a protein (P) and a ligand (L) according to C ⇌ P+L the corresponding dissociation constant is defined as $$K_d = \frac{[P][L]}{[C]},$$

where [P], [L] and [C] represent the concentrations of the protein, ligand and complex, respectively.

$K_d$, within the context of the present invention, is determined by the use of surface plasmon resonance technology, e.g. using the Biacore® instrument. Kd is determined in an experiment wherein the TNFα binding domain is immobilized on a sensor chip of the instrument, and samples containing TNFα prepared by serial dilution are passed over the chip. The skilled person may than interpret the obtained sensograms to establish the Kd value (the apparent Kd value) for the interaction of TNFα binding domain and TNFα. Apparent Kd are calculated from the results, using the 1:1 Langmuir binding model of the BIAevaluation 3.2 software provided by the instrument manufacturer, according to the manufacturer's instructions.

Kd, according to the invention is preferably measured for the free protein construct, i.e., the protein of the invention in a state not bound to the surface of the producing microorganism. In another embodiment Kd is measured for the protein bound to the surface of the microorganism.

A "surface attachment domain" of a protein, according to the present invention, shall be understood as being any domain of said protein which is capable of attaching the said protein to the surface of a microorganism, e.g., the microorganism producing the protein. In preferred embodiments, the surface attachment domain comprises a lipobox and preferably a corresponding signal peptide (anchoring to membrane via a lipid group), or at least one LysM repeat (sometimes also referred to as a peptidoglycan binding domain, PBD), at least one choline binding domain (CBD) or at least one LPxTG motif (cell wall binding domain). A surface attachment domain of the invention preferably comprises at least one of the following consensus sequences:

LysM repeat consensus sequence: [YV]-$X_{(0-4)}$-G-D-[ST]-[VLIA]-$X_{(0-2)}$-[VLIA] (SEQ ID NO. 17).

CBD consensus sequence: G-$X_{(0-5)}$-G-X-[WYI]-[WYT]-[YVL]-[FV] (SEQ ID NO. 18).

Lipobox consensus sequence (+signal peptide): M-$X_{(1-10)}$-[RK]-$\{DERK\}_{(7-17)}$-[LVTIMG]-[ASTIVGMLCPFL]-[AGLISVTFP]-C (SEQ ID NO. 19).

LPxTG consensus sequence: L-P-X-T-G (SEQ ID NO. (20).

in which X denotes any naturally occurring amino acid, and in which square brackets indicate one position which can be filled with any of the amino acids indicated between the square brackets. Rounded brackets ("{ . . . }") indicate a position which can be filled with any amino acid except the ones mentioned between the rounded brackets. The numbers in subscript "$_{(X-Y)}$" indicate that the corresponding amino acid is repeated the indicated number of times, i.e., from X to Y. Preferred surface attachment domains comprise LysM repeats.

"LysM repeats" (or "Lysin motifs") are well known in the art. More than 4000 proteins of both prokaryotes and eukaryotes have been found to contain one or more LysM repeats. Notably, this collection contains not only truly secreted proteins, but also (outer-) membrane proteins, lipoproteins or proteins bound to the cell wall in a (non-) covalent manner. LysM repeats typically range in length from 40 to 65 amino acid residues and binds to various types of peptidoglycan and chitin, recognizing the N-acetylglucosamine moiety. Most bacterial LysM-containing proteins are peptidoglycan hydrolases with various cleavage specificities. LysM repeats occur frequently in bacterial lysins, in bacteriophage proteins and in certain proteins of eukaryotes (Pfam PF01476 and Prodom PD407905). They are also present in bacterial peptidoglycan hydrolases and in peptidases, chitinases, esterases, reductases or nucleotidases. Multiple LysM repeats within one surface attachment domain are separated by spacing sequences mostly consisting of Ser, Thr and Asp or Pro residues, which may form a flexible region between the LysM repeats. The intervening sequences vary in length, composition and do not share significant homology. LysM repeats are present in the N-terminal as well as the C-terminal domains of proteins; they are also present in the central part of proteins, possibly connecting two (catalytic) domains. Prokaryotic LysM repeats, in contrast to their eukaryotic counterparts, do not possess possible disulphide bridges. Their domains contain extensive secondary structures and hydrogen bond networks, and consequently, disulphide bridges are non-essential for their structure and functions. The isoelectric points (pls) of the LysM proteins range from 4 to 12, with most having a pl of 5 or 10. The best-characterized LysM-repeat containing protein is the N-acetylglucosaminidase AcmA of *L. lactis*. AcmA binds in a non-covalent manner to the cell wall and is responsible for cell lysis of producing cells.

In a preferred embodiment, the LysM repeat comprises the consensus sequence [YV]-$X_{(0-4)}$-G-D-[ST]-[VLIA]-$X_{(0-2)}$-[VLIA] (SEQ ID NO. 17).

The expression "to express on its surface", in relation to microorganisms expressing proteins, shall be understood to include microorganisms which express the protein, secrete the protein into the surrounding medium, wherein the protein is subsequently attached to the surface of the microorganism by means of covalent or non-covalent attachment.

"GRAS", in respect to a microorganism within the context of the present invention, shall be understood to be a microorganism which is generally regarded as safe in accordance with the US Food And Drug Administration guidelines. The expression "GRAS microorganism" and "food grade organism" can be used interchangeably. A GRAS microorganism is a microorganism that has a long history of safe usage and is a constituent of fermented foods. Such microorganisms have "generally recognized as safe" status. Preferably genetically modified microorganism of food grade strain relates to lactic acid bacteria. Lactic acid bacteria are a group of phylogenetically related microorganisms. Preferred GRAS organisms are: *Carnobacterium, Enterococcus, Lactobacillus, Lactococcus, Leuconostoc, Oenococcus, Pedicococcus, Streptococcus, Tetragenococcus, Vagococcus* and *Weisela*. According to their physiological characteristics, genus *Bifidobacterium* spp. is usually classified as lactic acid bacterium because it occupies the same environmental niches, even though it is phylogenetically more distant. Preferably genetically modified microorganism of food grade strain is *Lactococcus* species. In one preferred embodiment said genetically modified organism is *Lactococcus lactis* strain.

Genetically modified GRAS microorganisms such as lactic acid bacteria with desirable new traits can be obtained by application of molecular biology techniques and production recombinant microorganism.

The "surface" of a microorganism, according to the invention, shall be understood to mean the outer surface of the cell wall of the microorganism.

A "homologue" of a reference protein, according to the invention, is a protein which has a similar, but not a fully identical amino acid sequence as the reference protein, and which has the same biological function or activity as the reference protein. The homologue has preferably an amino acid sequence which is 50, 70, 80, 90, 95, or 99% identical to the amino acid sequence of the original protein.

Within the context of the present invention, the "% identity" of a protein relative to a reference protein of a defined length shall be understood as follows: A peptide that is 50 percent identical to a reference polypeptide that is 100 amino acids long can be a 50 amino acid polypeptide that is completely identical to a 50 amino acid long portion of the reference polypeptide. It might also be a 100 amino acid long polypeptide, which is 50 percent identical to the reference polypeptide over its entire length. Of course, other polypeptides will meet the same criteria. The term "sequence identity" as used herein means that the sequences are compared as follows. The sequences are aligned using Version 9 of the Genetic Computing Group's GAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the reference polypeptide.

To achieve anchoring in the extracellular site of cell membrane, TNFα binding domain is expressed as fusion protein containing signal peptide for extracellular secretion, TNFα binding domain and surface attachment domain. Signal peptide leads the fusion protein into the extracellular space, where surface attachment domain anchors it on the membrane by binding to peptidoglycan. Signal peptide is processed and detached from fusion protein when reaching extracellular space.

Quantitative measure of affinity (Kd) may be determined also for mentioned isolated fusion protein with signal peptide detached by using surface plasmon resonance. Said fusion protein may be isolated from the growth medium using methods known to the person skilled in the art and immobilized on a sensor chip e.g. of the Biacore® instrument. Samples containing TNFα prepared by serial dilution are passed over the chip. The skilled person may than interpret the obtained sensograms to establish a quantitative measure, apparent Kd value for the interaction of fusion protein and TNFα. Apparent Kd values may then be calculated from the results, using e.g. the 1:1 Langmuir binding model of the BIAevaluation 3.2 software provided by the instrument manufacturer.

A genetically modified microorganism expressing TNFα binding domain on its surface, may be prepared by introduction of gene construct to the mentioned microorganism. The gene construct comprises secretion signal peptide coding sequence, TNFα binding domain coding sequence and surface attachment domain coding sequence, wherein the TNFα binding domain coding sequence and the surface attachment domain coding sequence are separated with a spacer region coding sequence. Said gene construct is under the control of suitable promoter. Gene construct may be a part of plasmid vector capable of replicating in said microorganism or may be introduced into the genome of said microorganism. Introduction of gene construct may be performed by electroporation.

The secretion signal peptide coding sequence codes for a secretion signal peptide. The secretion signal peptide enables the secretion of protein construct from the cell to the growth medium. Such secretion signal peptides include, but are not limited to signal peptide of Usp45 protein ($SP_{usp45}$), SP310 signal peptide and its improved mutants. Other secretion signal peptides are known in the art. Secretion may be increased by the use of synthetic pro-peptides. Such pro-peptides are homologues which contain acidic or neutral amino acids at position +2 and +8 or acidic amino acids at position +4 and +5 and have neutral or positive global net charge. Such propeptides include but are not limited to LEISSTCDA (SEQ ID NO. 14), LEISSYCDA (SEQ ID NO. 13), LQVDDIPSA (SEQ ID NO. 15) and LGISSTCNA (SEQ ID NO. 16). Preferably the secretion signal peptide is the signal peptide of Usp45, where the second amino acid K is changed to A and is straightened by the synthetic pro-peptide LEISSYCDA (SEQ ID NO. 13).

The usp45 gene encodes the major extracellular protein from *Lactococcus* lactis. The deduced sequence of the 27 residue leader peptide reveals the tripartite characteristics of a signal peptide. This leader peptide enables efficient secretion of various proteins. The Usp45 protein, according to the invention, is the one accessible in GenBank under the following GenBank record:

| | |
|---|---|
| LOCUS | LACUSP45, 1592 bp, DNA, linear, BCT 26-APR-1993 |
| DEFINITION | *L. lactis* secreted protein (usp45) gene, complete cds. |
| ACCESSION | M60178 M35374 X53491 |
| VERSION | M60178.1 GI: 149524 |
| KEYWORDS | secreted protein. |
| SOURCE | *Lactococcus lactis* subsp. *cremoris* MG1363 |
| ORGANISM | *Lactococcus lactis* subsp. *cremoris* MG1363<br>Bacteria; Firmicutes; Lactobacillales; Streptococcaceae; *Lactococcus*. |
| REFERENCE | 1 (bases 1 to 1592) |
| AUTHORS | van Asseldonk, M., Rutten, G., Oteman, M., Siezen, R. J., de Vos, W. M. and Simons, G. |
| TITLE | Cloning of usp45, a gene encoding a secreted protein from *Lactococcus lactis* subsp. *lactis* MG1363 |
| JOURNAL | Gene 95 (1), 155-160 (1990) |

The Usp45 protein is thus understood to be the protein having the amino acid sequence of SEQ ID NO:12. First 27 amino acids represent a preferred signal peptide $SP_{usp45}$. The protein product of mentioned gene construct is secreted to the medium and from there attached to the surface of said microorganism by binding to peptidoglycan. The attachment to the peptidoglycan on cell surface may be non-covalent, where protein construct comprises different number of peptidoglycan binding domains derived from C terminal part of AcmA protein. The attachment to the peptidoglycan on cell surface may be covalent. This may be achieved by addition of LPXTG (SEQ ID NO. 20) signal peptide to the protein construct to be covalently attached to the cell surface peptidoglycan. The attachment of such assembly to surface peptidoglycan is catalysed by enzyme sortase. Surface attachment domain coding sequence preferably codes for different number of peptidoglycan binding domains derived from C terminal part of AcmA. Preferably surface attachment domain consists of one to six LysM repeats. More preferably it consists of two to four LysM repeats, more preferably of three LysM repeats.

Spacer region coding sequence between TNFα binding domain coding sequence and surface attachment domain coding sequence may be derived from AcmA protein. The length of spacer region may be 5-50 amino acids, preferably 10-30, more preferably 20 amino acids.

The AcmA protein, according to the invention, is the one accessible in GenBank under the following GenBank record:

| | |
|---|---|
| LOCUS | AF036720, 2379 bp DNA linear BCT 31-DEC-1997 |
| DEFINITION | *Lactococcus lactis* N-acetylmuramidase (acmA) gene, complete cds. |
| ACCESSION | AF036720 |
| VERSION | AF036720.1 GI: 2707291 |
| KEYWORDS | . |
| SOURCE | *Lactococcus lactis* |
| ORGANISM | *Lactococcus lactis*<br>Bacteria; Firmicutes; Lactobacillales; Streptococcaceae; *Lactococcus*. |
| REFERENCE | 1 (bases 1 to 2379) |
| AUTHORS | Pillidge, C. J. |
| TITLE | Nucleotide sequence of N-acetylmuramidase gene acmA from *Lactococcus lactis* subsp. *cremoris* 2250 |
| JOURNAL | Unpublished |
| REFERENCE | 2 (bases 1 to 2379) |
| AUTHORS | Pillidge, C. J. |
| TITLE | Direct Submission |
| JOURNAL | Submitted (02-DEC-1997) New Zealand Dairy Research Institute, Private Bag 11029, Palmerston North, New Zealand |

The AcmA protein is thus understood to be the protein having the amino acid sequence of SEQ ID NO:11.

Examples of described gene constructs of the invention are shown in sequence listing as SEQ ID NO:6 to SEQ ID NO:10 and in FIGS. 7*a* and 7*b*.

The promoter that controls the expression of mentioned gene construct may be constitutive or inducible. Constitutive promoters enable continuous protein production, but are usually prone to lower level of expression. Inducible promoters are also referred to as controlled promoters. Inducible promoters usually provide higher expression level. Inducible promoters include but are not limited to bacteriocin controlled promoters, carbohydrate controlled promoters, pH controlled promoters, phage promoter Φ31 and temperature controlled promoters.

Bacteriocin controlled promoters are controlled by addition of bacteriocins. Such bacteriocins include, but are not limited to nisin and pediocin. pH controlled promoters may be $P_{170}$, induced by accumulation of lactic acid at pH 6.0-6.5, $P_{gad}$, induced by chloride ions and $F_1F_0$-ATPase promoter, induced by acidification. Temperature controlled promoter may be $P_2$, where inactivation of repression is achieved at temperatures above 40° C. Carbohydrate promoters may be lacA and xylA operons that are induced by changing the carbon source in the growth medium.

Anti-TNFα binding domain displaying microorganism binding to TNFα refers to a property which may be tested by the use of flow cytometry or confocal microscopy. The testing of binding of surface expressed peptide to TNFα in accordance with invention is described in examples.

According to another embodiment the present invention relates to the use of anti-TNFα peptide displaying microorganism for the purpose of reducing the content of free TNFα in gastrointestinal tract.

A genetically modified microorganism of the invention can be used as medicament to treat IBD. Said disease or disorder is characterized by imbalance in TNFα production, and can be treated by TNFα inactivating compounds, such as TNFα binding polypeptide expressed on the surface of genetically modified microorganisms. More preferably, said disease is an irritable bowel disease, including but not limited to chronic colitis, ulcerative colitis and Crohn's disease.

Another embodiment of the present invention is the pharmaceutical composition for treating IBD. Preferably pharmaceutical composition, comprising anti-TNFα peptide displaying microorganisms is for oral administration.

The pharmaceutical composition may be liquid, comprising microorganism expressing anti TNFα peptide on surface, or it may be solid, comprising dried microorganism that can be reactivated when put in a suitable environment. Microorganisms may be dried by any system, including freeze drying and spray drying. "Anti-TNFα peptide displaying microorganism" as used here, means that the microorganism is viable and can express anti-TNFα peptide when placed in a suitable environment, not necessarily expressing the anti-TNFα peptide in the pharmaceutical composition. The pharmaceutical composition may further comprise agents known to the person skilled in the art to improve viability of the microorganisms and stability of surface expressed anti-TNFα peptide, such as but not limited to skimmed powdered milk.

Lactic acid bacteria thrive in nutrient rich environments such as milk. They are integral part of mammalian GI flora and are considered beneficial to human health. As such they are added to the diet in the form of probiotic food. The present invention also relates to a food containing such recombinant microorganisms. Food composition may be milk, yogurt, curd, cheese, fermented milks, milk based fermented products, ice cream, fermented cereal based products and milk based powders.

The present invention further relates to a system for immobilization of a heterologous protein construct containing a TNFα binding polypeptide coupled to a surface attachment domain on the cell surface of microorganisms, preferably a GRAS microorganism, in cases for which the use of genetically modified bacteria is less desirable. For example, in applications that involve uncontrolled release into the environment, and foods products. This system is based on non-genetically modified GRAS microorganisms, which are used as carrier (support) to bind an externally added heterologous protein construct of the invention. The binding of the protein construct is preferably by a surface attachment domain as described above. Thus the expressed protein construct is not anchored or attached to the producing cells. The cells for production of the protein construct of the invention and the carrier cells may be different, thereby allowing the use of a non-genetically modified (non-GMO) cells as carrier cells.

Preferred GRAS non-GMO carrier cells are: *Carnobacterium, Enterococcus, Lactobacillus, Lactococcus, Leuconostoc, Oenococcus, Pedicococcus, Streptococcus, Tetragenococcus, Vagococcus, Weisela* and *Bifidobacterium* spp. Preferably non-GMO carrier microorganism strain is *Lactococcus* species. In one preferred embodiment said non-GMO carrier microorganism is *Lactococcus lactis* strain.

Non-GMO carrier microorganisms may be viable or non-viable (i.e., they cannot proliferate). Such non-viable cells can be generated various methods known in the art, such as UV, chemical inactivation, heat and gamma-irradiation. Preferably non-viable non-GMO carrier microorganisms are prepared by boiling in various acids, for example trichloroacetic acid.

Protein constructs of the invention, composed of signal peptide for extracellular secretion, TNFα binding domain and surface attachment domain, are expressed in a recombinant expression host. Protein constructs are then secreted in the growth medium. The protein construct may be purified from growth medium or cell free growth medium may be added to non-GMO carrier microorganism. Protein constructs of the invention composed of the TNFα binding domain and anchoring domain (i.e., lacking the secretion signal peptide) may be expressed intracellularly in a recombinant expression host. The protein construct is then purified from host cell lysate and added to the non-GMO carrier microorganism.

Recombinant expression host is a system suitable for the production of a protein construct of the invention, such as bacterial expression systems, yeast expression systems, baculovirus/insect expression systems, and/or mammalian cells.

The expression system preferably includes an expression vector, including the DNA encoding the protein construct of the invention, and the host cell. The expression system preferably allows foreign gene expression at a high level. Preferred recombinant GRAS microorganisms are lactic acid bacteria (e.g., *L. lactis*) for use as an expression host. In this case the cell free culture medium is directly suitable for addition to non-GMO carrier microorganism and further purification steps are not necessary.

The use of a non-GMO carrier microorganism is demonstrated in Example 6.

EXAMPLE 1

Design of Gene Constructs for Lactococcal Surface Display

Several gene constructs were prepared to obtain fusion protein with optimal surface binding capabilities and are shown on FIG. 7*a* schematically. They are composed of three functional parts: signal sequence for the secretion to the growth medium, binding domain and peptidoglycan binding domain for surface attachment. Secretion signal was derived from Usp45 protein and was strengthened by synthetic propeptide LEISSYCDA (SEQ ID No: 13) in all constructs except pSDBA1. Binding domains were either immunoglobulin-binding B domain, or TNFα-binding Z domain.

Immunoglobulin-binding B domain served as model binding domain to characterize expression and functionality of the construct.

Peptidoglycan binding domains were derived from AcmA protein. They consisted of one peptidoglycan binding LysM repeat, as in the case of pSDBA1 or pSDLBA1, or three peptidoglycan binding LysM repeats in remaining constructs. pSDLBA3a, pSDLBA3b and pSDLBA3c contained three peptidoglycan binding LysM repeats with variable length of spacer region between binding domain and first LysM repeat.

Bacterial Strains, Media and Culture Conditions

Bacterial strains used in this study are shown in Table 1. *E. coli* DH5α was grown at 37° C. with aeration in LB medium supplemented with 100 μg/ml ampicillin.

*L. lactis* NZ9000 and *L. lactis* NZ9000ΔHtrA were grown in M-17 medium supplemented with 0.5% glucose at 30° C. without aeration. 10 μg/ml of chloramphenicol or erythromycin or both was added when appropriate.

DNA Manipulation and Plasmid Construction

General cloning procedures were performed using conventional molecular biology methods. Electroporation of *L. lactis* was performed, using Gene Pulser II apparatus. Primers and plasmids are listed in Table 1.

AcmA1, acmA3a, acmA3b and acmA3c genes were amplified from lactococcal genomic DNA using colony PCR with AcmA-EcoRI/AcmA-XbaI, AcmA-EcoRI/AcmA-R3-XbaI, AcmA-Fb-EcoRI/AcmA-R3-XbaI and AcmA-Fc-EcoRI/AcmA-R3-XbaI primer pairs, respectively. SpUsp45 was amplified from pGEM::Usp using Usp1-NcoI/UspR-BamHI primer pair. B domain gene was amplified from pGEM::B using Bdom-F-BamHI/ Bdom-R-EcoRI primer pair. PCR amplicons were digested with restriction enzymes in the following manner: spUsp45 with BamHI, b-dom with BamHI and EcoRI and acmA1 with EcoRI. Digested fragments were ligated and fusion gene termed sdb was PCR amplified using Usp1-NcoI/AcmA-XbaI primer pair. Sdb was digested with NcoI and XbaI and cloned to equally prepared pNZ8148, yielding pSDBA1. LEISSYCDA synthetic propeptide gene was added to spUsp45 gene by PCR using Usp1-NcoI/LeisR-BamHI primer pair and pGEM::Usp as a template, yielding spUsp45-LEIS. SpUsp45-LEIS gene was used to substitute spUsp45 in pSDBA1 via NcoI/BamHI restriction sites, yielding pSDLBA1. AcmA3a, acmA3b and acmA3c genes were used to substitute acmA1 gene in pSDLBA1 via EcoRI/XbaI restriction sites, yielding pSDLBA3a, pSDLBA3b and pSDLBA3c, respectively. TNFα binding Z domain gene labeled z-tnf, with BamHI and EcoRI restriction sites was designed on the basis of Z00185 polypeptide described in WO2006/092338 by codon optimization and ordered from ATG:biosynthetics. Z-tnf was BamHI/EcoRI digested and substituted b-dom in equally prepared pSDLBA3a, yielding pSDZ-TNF. All the constructs are shown in FIG. 7*a*.

Expression of Fusion Proteins in *L. lactis*

Overnight cultures of *L. lactis* NZ9000 or NZ9000ΔHtrA harboring appropriate plasmid: pSDBA1, pSDLBA1, pSDLBA3a, pSDLBA3b, pSDLBA3c or pSDZ-TNF, were diluted in 10 ml of fresh GM-17 medium, grown to optical density $A_{600}$=0.5-0.8 and induced with 25 ng/ml nisin. 3 hours after induction we split the culture in half. 5 ml were centrifuged at 5000 g for 10 min. Supernatant was decanted; cell pellet was resuspended in 0.1 M potassium phosphate buffer pH 7.00.

EXAMPLE 2

Surface Display of Model B Domain, Characterization of Secretion, Optimization of Protein Yield and its Functionality
SDS PAGE and Western Blot SDS PAGE was performed using a mini-Protean II apparatus. Prestained standards were used for molecular weight comparison. Protein concentration was determined by Bio Rad protein assay and equal amounts were used to enable comparison between samples. Samples were denatured by heating at 100° C. in the presence of DTT before loading. Proteins were stained with Coomassie Brilliant Blue or transferred to polyvinylidene fluoride membrane. The membrane was blocked in 1% Western blocking solution and incubated overnight at 4° C. with FITC conjugated anti-protein A antibody. After washing with 50 mM Tris-HCl, 150 mM NaCl, 0.05% Tween 20, pH 7.5, the fluorescence was detected with Typhoon 9410 imager using blue excitation at 488 nm.

Expression of fusion proteins was confirmed by Western blot using FITC conjugated anti-protein A antibody, which bound the B domain of the fusion proteins. Cell lysate, containing cytoplasmic and surface bound fusion protein, and growth medium, containing secreted unbound fusion protein, were tested. All fusion proteins were detected in both, cell lysate and growth medium, and their observed molecular weights corresponded to the calculated. Molecular weight of fusion proteins was: Sdba1 18.4 kDa, Sdlba1 19.4 kDa, Sdlba3a 34.0 kDa, Sdlba3b 32.9 kDa and Sdlba3c 31.8 kDa.

Two bands of similar size were detected with all fusion proteins, which corresponded to fusion proteins with or without secretion signal with calculated molecular weight difference of 2.9 kDa.

N-Terminal Sequencing

The processing of secretion signals was evaluated with growth medium fraction of Sdba1 and Sdlba1 proteins. Their N-terminal sequence was determined to be GSADN and LEISS, respectively, which corresponds to the N-terminal sequences of fusion proteins without Usp45 signal.

Growth media of *L. lactis* NZ9000 expressing Sdba1 or Sdlba1 were concentrated on Amicon Ultra-4, separated on SDS PAGE and blotted to PVDF membrane. Membrane was stained briefly with Coomassie Brilliant Blue, dried and corresponding bands were excised. N-terminal amino acid sequences of Sdba1 and Sdlba1 were determined by automated Edman degradation using an Applied Biosystems 492 Protein sequencer.

Staining of Cells, Flow Cytometry and Fluorescent Microscopy

Surface display of B domain was characterized by flow cytometry and fluorescent microscopy. Control and Sdlba3b-expressing cells stained with unspecific antibodies were visualized using fluorescent microscopy. Stronger binding of antibodies and increased fluorescence was observed with Sdlba3b-expressing cells.

Figure 2A:
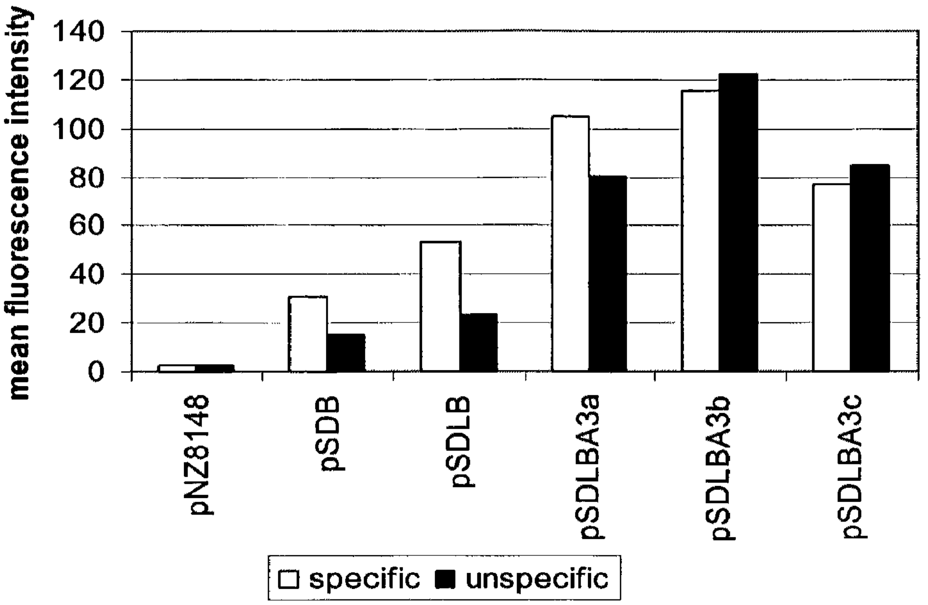
FIGS. 2*a* and 2*b* show the results of flow cytometry of lactococcal cells harboring different plasmids.
Figure 2B:
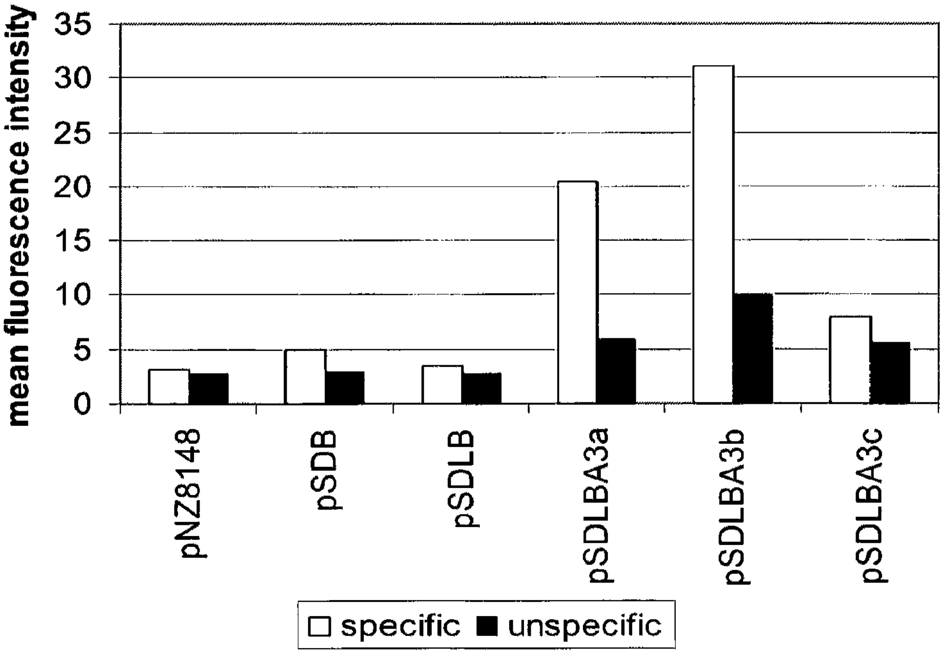
Figure 3:
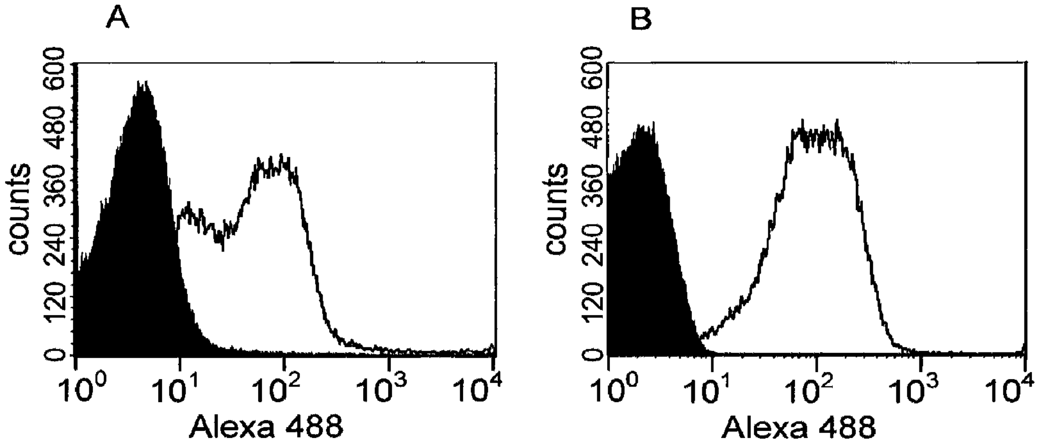
FIG. 3 shows a shift in fluorescence determined by flow cytometry.

For flow cytometric analysis, cells were gated as shown in FIG. 1. All constructs for surface display of B domain were analyzed and compared. Anti-protein A antibody was used to specifically detect and quantify surface-bound fusion protein and unspecific rabbit anti-mouse antibodies were used to evaluate the B domain's capability to bind Fc region of immunoglobulins. The results are presented as mean fluorescence intensity values of lactococcal cells, transformed with different plasmids and stained with specific or unspecific antibody for both NZ9000 strain in FIG. 2*a* and NZ9000ΔHtrA strain in FIG. 2*b*. Fluorescence correlates with the amount of surface-bound fusion protein. The expression of SdlbA3b resulted in the highest responses with both specific and unspecific antibody in both bacterial strains. NZ9000 strain showed superior results in comparison to NZ9000ΔHtrA in the initial experiments. For more detailed comparison between pNZ8148; control and pSDLBA3b-containing cells stained with specific and unspecific antibody is shown in FIGS. 3 A and 3 B, respectively. A distinct shift in fluorescence between controls (back fill) and Sdlba3b-expressing cells (black line) can be observed in both cases.

FIG. 3 A shows control and Sdlba3b-expressing cells detected with specific FITC-conjugated antibodies. Mean fluorescence intensity for control is 2.61 and for the sample 115.70. FIG. 3 B shows control and B domain-expressing cells detected with unspecific Alexa Fluor 488-conjugated antibodies. Mean fluorescence intensity for control is 2.26, and for the sample 150.71.

For the flow cytometric analysis 10 μL of cell cultures, approximately $10^7$ cells/ml, were added to 500 μL of 50 mM Tris-HCl, 150 mM NaCl, pH 7.5 and centrifuged 3 min at 5000 g at 4° C. Supernatants were decanted and cells were resuspended in 500 μL of the same buffer. Next, either 1 μg of specific, FITC conjugated anti-protein A antibody or 2 μg of unspecific, Alexa Fluor 488 conjugated rabbit anti-mouse antibody was added to the suspensions and incubated 2 hours at RT with constant shaking at 100 rpm. Cells were than washed three times with 200 μL 50 mM Tris-HCl, 150 mM NaCl, 0.1% Tween 20, pH 7.5 and resuspended in 500 μt of 50 mM Tris-HCl, 150 mM NaCl, pH 7.5. Stained sample and control cells were analyzed with FACS Calibur flow cytometer. At least 100000 bacterial cells were counted for each sample. Cells were gated using FSC vs. SSC to isolate the bacterial cells.

For the purpose of fluorescent microscopy the staining protocol was similar except the starting volume of cell cultures was 20 μL and final volume of TBS buffer (50 mM Tris-HCl, 150 mM NaCl, pH 7.5) for re-suspension was 200 μL. Fluorescence microscopy was performed using a Carl Zeiss LSM 510 confocal microscope. Alexa Fluor 488 was excited with an argon laser, and emission was filtered using narrow-band 505-530 nm filter. Images were analyzed using Carl Zeiss LSM image software 3.0.

EXAMPLE 3

Figure 4:
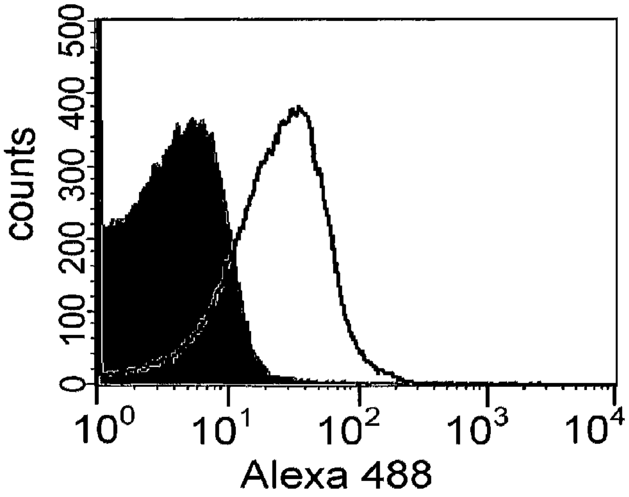
FIG. 4 shows a shift in fluorescence; control and Sdz-tnf-expressing cells detected with Alexa Fluor 488-conjugated TNFα.

Surface Display of TNFα-Binding Z Domain and its Functionality
Staining of Cells, Flow Cytometry and Fluorescent Microscopy Surface display of TNFα-binding Z domain was characterized by the capability to bind Alexa Fluor 488-conjugated TNFα. FIG. 4 shows flow cytometry results. Control contains pNZ8148 and is shown in black fill. Cells containing pSDZ-TNF are shown with black line. A distinct shift in fluorescence can be observed. Mean fluorescence intensity for control is 4.83 and for the sample 150.71.

Stronger fluorescence of Sdz-tnf-expressing cells was also observed with the use of fluorescent microscopy.

For flow cytometric analysis and fluorescent microscopy samples were prepared as described in example 2, except 10 μL of Alexa 488-labelled TNFα was added to the suspensions.

Soluble TNFα was labelled using Alexa Fluor 488 Microscale Protein Labeling kit according to manufacturer's protocol. Final concentration of labeled protein was 0.5 mg/ml determined with Nanodrop 1000 Spectrophotometer.

EXAMPLE 4

Stability of Surface Displayed Model B Domain in Simulated Gastric Conditions

Stability of the surface displayed B domain was tested against simulated gastric juice. 500 μl of pNZ8148 as control or pSDLBA3b-containing cells were mixed with either 500 μl of TBS buffer, pH 7.0 or 500 μl of simulated gastric juice, which was prepared using 3 mg/ml pepsin and pH was adjusted to 2.0 or 4.0 with concentrated HCl. The mixture was than incubated at room temperature for 30 min. 50 μl of the mixture was washed with 500 μl of TBS buffer, stained with Alexa Fluor 488 rabbit anti-mouse antibody and analyzed with flow cytometer as described earlier.

Capability of surface displayed B domain to bind Fc region of antibody was tested after the incubation of cells containing pSDLBA3b in simulated gastric conditions and compared to incubation at pH 7.0; positive control or to cells containing pNZ8148 at pH 7.0; negative control.

Figure 5:
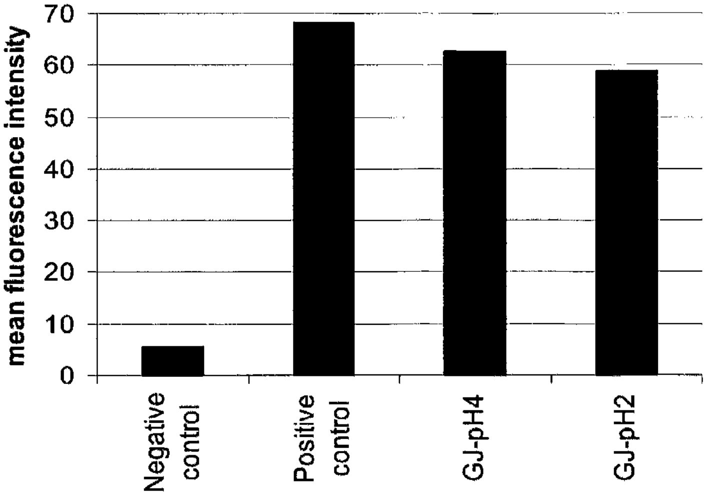
FIG. 5 shows the loss of fluorescence intensity in samples, exposed to simulated gastric juice, as determined by flow cytometry.

The loss of fluorescence intensity in samples, exposed to simulated gastric juice was less than 14% even after 30 min at pH 2.0 as shown in FIG. 5.

EXAMPLE 5

Determination of Maximum Unspecific Antibody Binding Capacity to B Domain-Displaying Cells Control cell cultures containing pNZ8148 or cell cultures containing pSDLBA3b were washed with PBS buffer twice and resuspended in PBS to the cell density of $1\times10^9$ cells/mL. 100 μL of cells were centrifuged and resuspended in 100 μl PBS containing M13/HRP antibody with various concentrations (0.45, 0.9, 1.8, 4.6 and 9.0 μg/mL) and incubated for 2 h at room temperature with constant shaking in preblocked Eppendorf tubes. After incubation, cells were pelleted and 20 μL of supernatant was transferred to microtiter plate and incubated with 180 μL TMB substrate for 15 minutes at room temperature. Colour development was terminated by the addition of 50 μL 2 M $H_2SO_4$ and absorbance was read at 450 nm using Rainbow reader. All samples were measured in duplicate. Amount of adsorbed antibody; Γ was calculated as follows: $\Gamma=C_{Ab}\times V\times(1-A_{450}(\text{pSDLBA3b})/A_{450}(\text{pNZ8148}))$. Langmuir adsorption isotherm was assumed for the adsorption of antibody to the surface of Sdlba3b-expressing *L. lactis*. Langmuir linear regression method ($C_{Ab}/\Gamma=C_{Ab}/\Gamma_{max}+1/(K\times\Gamma_{max})$) was used to fit the Langmuir equation to the data and maximal amount of adsorbed antibody; $\Gamma_{max}$ was calculated.

Figure 6:
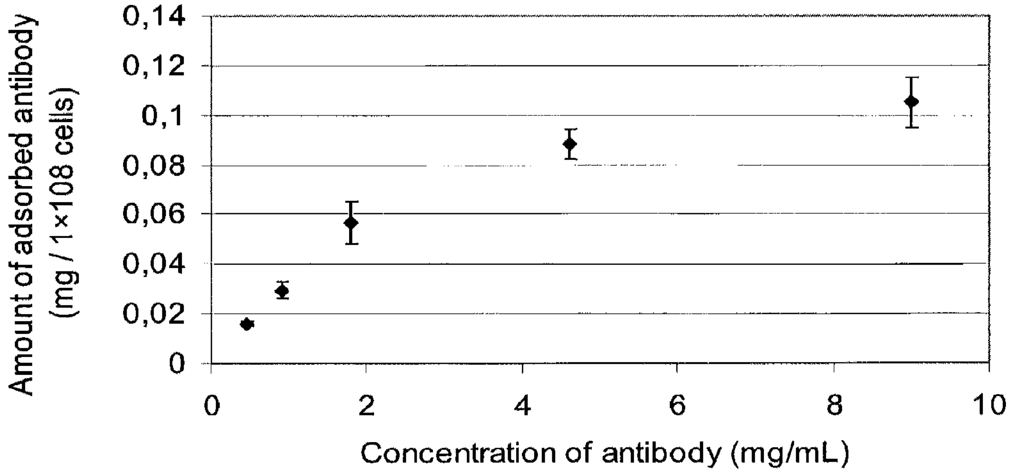
FIG. 6 shows unspecific adsorption of antibody to B domain displaying cells.

The amount of antibody adsorbed on $1\times10^8$ cells was calculated and plotted against the concentration of antibody, shown in FIG. 6.

Langmuir linear regression method was applied and yielded the equation $C_{Ab}/\Gamma=6,837\times C_{Ab}+22,688$ ($r^2=0.9897$). From this equation, the maximum amount of adsorbed antibody was calculated to be 0.146 μg per $1\times10^8$ cells.

EXAMPLE 6

Immobilization of Heterologous Protein Constructs Containing TNFα-Binding Z Domain or Fc-Binding B Domain on Non-GMO Carrier Microorganism *L. lactis*

Overnight cultures of *L. lactis* NZ9000 harboring plasmid pSDLBA3a or pSDZ-TNF were diluted in 10 ml of fresh GM-17 medium, grown to optical density $A_{600}=0.5-0.8$ and induced with 25 ng/ml nisin. Three hours after induction cultures were centrifuged at 5000 g for 10 min. Supernatant containing secreted protein construct was separated from the cells and filtered through 0.22 μm Minisart filter (Sartorius). Overnight culture of non-recombinant carrier microorganism *L. lactis* NZ9000 was grown in fresh GM-17 medium and centrifuged. Supernatant was separated from cells.

500 μL of cell-free supernatant from culture expressing either TNFα-binding fusion peptide or Fc-binding fusion peptide were added to approximately $10^7$ of non-recombinant *L. lactis* cells and incubated for 2 h at room temperature. Next, cells were separated from supernatants by 3 min centrifugation at 5000 g and resuspended in 500 μL of TBS. Next, either 10 μL of Alexa 488-labelled TNFα or 2 μg of Alexa Fluor 488 conjugated rabbit anti-mouse antibody (Invitrogen; A-11059) was added to the suspensions and incubated 2 hours at room temperature with constant shaking at 100 rpm. Cells were than washed three times with 200 μL 0.1% TBST and resuspended in 500 μL of TBS. For control, non-recombinant *L. lactis* without previous incubation with cell-free supernatants from culture expressing either TNFα-binding fusion peptide or Fc-binding fusion peptide were stained as described. Stained sample and control cells were analyzed with FACS Calibur (Becton Dickinson Inc.) flow cytometer. At least 100,000 bacterial cells were counted for each sample. Cells were gated using FSC vs. SSC to isolate the bacterial cells.

Figure 8:
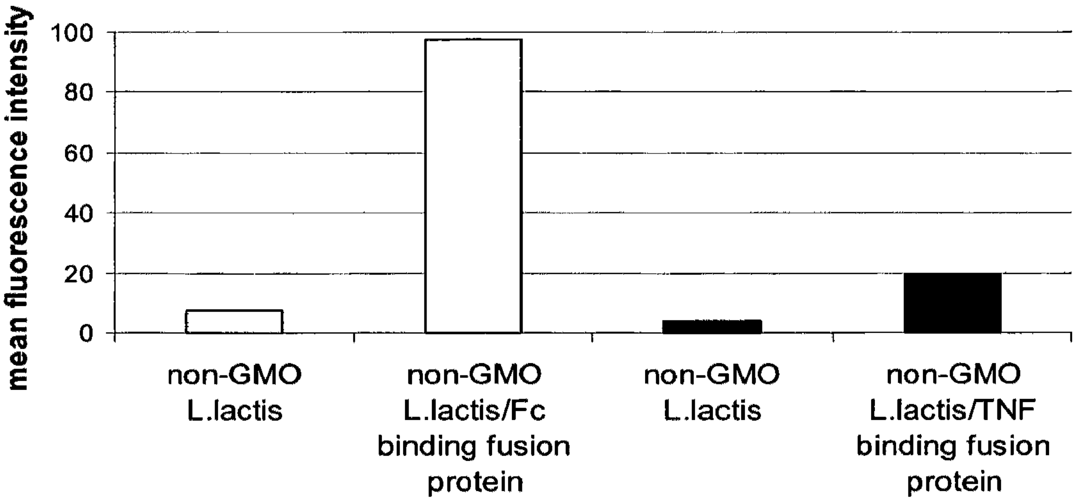
FIG. 8 shows successful immobilization of heterologous protein constructs containing TNFα-binding Z domain or Fc-binding B domain on non-GMO carrier microorganism *L. lactis* stained with Alexa 488-labelled TNFα (black bars) or 2 μg of Alexa Fluor 488-labelled conjugated rabbit anti-mouse antibody (grey bars).

The results are shown in FIG. 8.

References

Hugot J P, Zouali H, Lesage S, Thomas G. Etiology of the inflammatory bowel diseases. Int J Colorectal Dis. 1999 February; 14(1):2-9.

Cho J H. The genetics and immunopathogenesis of inflammatory bowel disease. Nat Rev Immunol. 2008 June; 8(6):458-66.

Schwartz M, Cohen R. Optimizing conventional therapy for inflammatory bowel disease. Curr Gastroenterol Rep. 2008 December; 10(6):585-90.

Old L J. Tumor necrosis factor (TNF). Science. 1985 Nov. 8; 230(4726):630-2.

Sandborn W J, Hanauer S B. Antitumor necrosis factor therapy for inflammatory bowel disease: a review of agents, pharmacology, clinical results, and safety. Inflamm Bowel Dis. 1999 May; 5(2):119-33.

de Silva D G, Mendis L N, Sheron N, Alexander G J, Candy D C, Chart H, Rowe B. TNF alpha in stool as marker of intestinal inflammation. Lancet. 1992 Aug. 8; 340(8815):372.

Worledge K L, Godiska R, Barrett T A, Kink J A. Oral administration of avian tumor necrosis factor antibodies effectively treats experimental colitis in rats. Dig Dis Sci. 2000 December; 45(12):2298-305.

Le Loir Y, Nouaille S, Commissaire J, Bretigny L, Gruss A, Langella P. Signal peptide and propeptide optimization for heterologous protein secretion in *Lactococcus lactis*. Appl Environ Microbiol. 2001 September; 67(9):4119-27.

Nygren P A. Alternative binding proteins: affibody binding proteins developed from a small three-helix bundle scaffold. FEBS J. 2008 June; 275(11):2668-76.

The invention claimed is:

1. A gene construct coding for a polypeptide comprising a secretion signal peptide, wherein said secretion signal peptide is a peptide sequence selected from LEISSYCDA (SEQ ID No: 13), LQVDDIPSA (SEQ ID No: 15) and LGISTCNA (SEQ ID No: 16), a TNFα binding domain and surface attachment domain for attachment to the surface of a lactic acid bacterium, said TNFα binding domain and said surface attachment domain being separated by a spacer region, said gene construct being under the control of a suitable promoter, wherein said TNFα binding domain is a TNFα binding affibody.

2. A gene construct according to claim 1, wherein said secretion signal peptide is a signal peptide of Usp45 or of a homologue having 95% sequence identity to Usp45.

3. A gene construct according to claim 1, wherein said surface attachment domain comprises 1 to 6 LysM repeats.

4. A gene construct of claim 1, said construct coding for the protein sequence (a) of any one of SEQ ID NO:6 to SEQ ID NO: 10, or (b) for a sequence which is at least 95% identical to any one of said sequences under (a).

5. A protein construct encoded by a gene construct of claim 1.

* * * * *